US011078220B2

(12) United States Patent
Drummond et al.

(10) Patent No.: US 11,078,220 B2
(45) Date of Patent: *Aug. 3, 2021

(54) HIGH-PURITY LARGE-SCALE PREPARATION OF STANNSOPORFIN

(71) Applicant: Mallinckrodt Hospital Products IP Limited, Dublin (IE)

(72) Inventors: George S. Drummond, New York, NY (US); Robert Caroselli, East Brunswick, NJ (US); Keith A. Cooke, Milton (CA); Daniel Levin, Toronto (CA); David G. Roe, Rockwood (CA); Christopher P. Boucher, Newmarket (CA)

(73) Assignee: Mallinckrodt Hospital Products IP Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/864,510

(22) Filed: May 1, 2020

(65) Prior Publication Data
US 2020/0255458 A1    Aug. 13, 2020

Related U.S. Application Data

(60) Continuation of application No. 16/298,603, filed on Mar. 11, 2019, now Pat. No. 10,662,209, which is a continuation of application No. 15/867,900, filed on Jan. 11, 2018, now Pat. No. 10,273,255, which is a division of application No. 15/343,967, filed on Nov. 4, 2016, now Pat. No. 9,902,745, which is a continuation of application No. 14/793,921, filed on Jul. 8, 2015, now Pat. No. 9,517,239, which is a continuation of application No. 14/460,080, filed on Aug. 14, 2014, now Pat. No. 9,107,927, which is a continuation of application No. 14/019,513, filed on Sep. 5, 2013, now Pat. No. 8,835,416, which is a continuation of application No. 12/968,651, filed on Dec. 15, 2010, now Pat. No. 8,530,458, which is a continuation of application No. 11/867,559, filed on Oct. 4, 2007, now Pat. No. 7,960,371.

(60) Provisional application No. 60/904,601, filed on Feb. 28, 2007, provisional application No. 60/849,641, filed on Oct. 4, 2006.

(51) Int. Cl.
C07D 487/22     (2006.01)
C07F 7/22       (2006.01)
C07F 7/00       (2006.01)
A61K 31/555     (2006.01)
A61K 9/00       (2006.01)

(52) U.S. Cl.
CPC .......... C07F 7/2284 (2013.01); A61K 9/0019 (2013.01); A61K 31/555 (2013.01); C07D 487/22 (2013.01); C07F 7/003 (2013.01)

(58) Field of Classification Search
CPC .................................................. C07F 7/2284
See application file for complete search history.

(56) References Cited

U.S. PATENT DOCUMENTS

| | | | |
|---|---|---|---|
| 4,619,923 A | 10/1986 | Kappas et al. | |
| 4,657,902 A | 4/1987 | Kappas et al. | |
| 4,668,670 A | 5/1987 | Rideout et al. | |
| 4,684,637 A | 8/1987 | Kappas et al. | |
| 4,692,439 A | 9/1987 | Rideout et al. | |
| 4,692,440 A | 9/1987 | Kappas et al. | |
| 4,708,964 A | 11/1987 | Allen | |
| 4,782,049 A | 11/1988 | Kappas et al. | |
| 4,831,024 A | 5/1989 | Vreman et al. | |
| 4,861,876 A | 8/1989 | Kessel | |
| 4,900,871 A | 2/1990 | Ellis, Jr. et al. | |
| 5,010,073 A | 4/1991 | Kappas et al. | |
| 5,062,775 A | 11/1991 | Orth | |
| 5,081,115 A | 1/1992 | Vreman et al. | |
| 5,162,313 A | 11/1992 | Kappas et al. | |
| 5,192,757 A | 3/1993 | Johnson et al. | |
| 5,223,494 A | 6/1993 | Kappas et al. | |
| 5,275,801 A | 1/1994 | Niedballa et al. | |
| 5,371,199 A | 12/1994 | Therien et al. | |
| 5,493,017 A | 2/1996 | Therien et al. | |
| 5,665,869 A | 9/1997 | Ryland et al. | |
| 5,756,723 A | 5/1998 | Therien et al. | |
| 5,817,830 A | 10/1998 | Therien et al. | |
| 5,883,246 A | 3/1999 | Bruckner et al. | |
| 5,886,173 A | 3/1999 | Hemmi et al. | |
| 5,889,181 A | 3/1999 | Kudrevich et al. | |
| 5,912,341 A | 6/1999 | Hoffman et al. | |
| 5,929,064 A | 7/1999 | Goel et al. | |
| 5,955,603 A | 9/1999 | Therien et al. | |
| 5,973,141 A | 10/1999 | Robinson et al. | |

(Continued)

FOREIGN PATENT DOCUMENTS

AU    2012202684 B2    7/2014
CA       2448570 A1   12/2002
(Continued)

OTHER PUBLICATIONS

Office Action and Search received for NO Patent Application No. 20091575, dated Jul. 27, 2020, 9 pages.

(Continued)

*Primary Examiner* — Paul V Ward

(74) *Attorney, Agent, or Firm* — Shook, Hardy & Bacon LLP

(57) ABSTRACT

Large scale (bulk) compositions comprising high-purity stannsoporfin are disclosed, as well as methods of synthesizing such compositions.

20 Claims, No Drawings

(56) References Cited

U.S. PATENT DOCUMENTS

| | | | |
|---|---|---|---|
| 5,990,363 | A | 11/1999 | Wijesekera et al. |
| 6,004,530 | A | 12/1999 | Sagner et al. |
| 6,066,333 | A | 5/2000 | Willis et al. |
| 6,114,321 | A | 9/2000 | Platzek et al. |
| 6,124,452 | A | 9/2000 | Dimagno |
| 6,177,561 | B1 | 1/2001 | Sinn et al. |
| 6,194,566 | B1 | 2/2001 | Platzek et al. |
| 6,235,895 | B1 | 5/2001 | McEwan et al. |
| 6,420,553 | B1 | 7/2002 | Inoue et al. |
| 6,462,192 | B2 | 10/2002 | Robinson et al. |
| 6,818,763 | B2 | 11/2004 | Vukovich et al. |
| 7,375,216 | B2 | 5/2008 | Vukovich et al. |
| 7,777,028 | B2 | 8/2010 | Vukovich et al. |
| 7,960,371 | B2 | 6/2011 | Drummond et al. |
| 8,178,664 | B2 | 5/2012 | Vukovich et al. |
| 8,530,458 | B2 | 9/2013 | Drummond et al. |
| 8,735,574 | B2 | 5/2014 | Boucher et al. |
| 8,835,416 | B2 * | 9/2014 | Drummond .......... A61K 31/555 514/185 |
| 9,107,927 | B2 | 8/2015 | Drummond et al. |
| 10,662,209 | B2 * | 5/2020 | Drummond ............... A61P 1/16 |
| 2003/0100752 | A1 | 5/2003 | Robinson |
| 2003/0225264 | A1 | 12/2003 | Vukovich et al. |
| 2004/0097481 | A1 | 5/2004 | Levinson et al. |
| 2004/0210048 | A1 | 10/2004 | Vukovich et al. |
| 2004/0224886 | A1 | 11/2004 | Chen et al. |
| 2006/0222668 | A1 | 10/2006 | Drummond et al. |
| 2006/0222669 | A1 | 10/2006 | Drummond et al. |
| 2007/0087933 | A1 | 4/2007 | Purta et al. |
| 2008/0113955 | A1 | 5/2008 | Levinson et al. |
| 2008/0125585 | A1 | 5/2008 | Drummond et al. |
| 2008/0154033 | A1 | 6/2008 | Vukovich et al. |
| 2008/0242857 | A1 | 10/2008 | Martin et al. |
| 2008/0261939 | A1 | 10/2008 | Drummond et al. |
| 2008/0280934 | A1 | 11/2008 | Lugtenburg et al. |
| 2010/0280237 | A1 | 11/2010 | Vukovich et al. |
| 2011/0082292 | A1 | 4/2011 | Drummond et al. |
| 2012/0253033 | A1 | 10/2012 | Boucher et al. |
| 2013/0158362 | A1 | 6/2013 | Tulloch et al. |
| 2014/0005380 | A1 | 1/2014 | Drummond et al. |
| 2014/0228560 | A1 | 8/2014 | Boucher et al. |
| 2015/0051184 | A1 | 2/2015 | Drummond et al. |
| 2016/0000802 | A1 | 1/2016 | Drummond et al. |

FOREIGN PATENT DOCUMENTS

| | | | |
|---|---|---|---|
| CA | 2665075 | A1 | 3/2014 |
| CA | 2665075 | C | 8/2014 |
| EP | 0199888 | B1 | 11/1986 |
| EP | 0527016 | A1 | 2/1993 |
| JP | S41-001622 | B | 2/1966 |
| JP | 58501130 | A | 7/1983 |
| JP | H01501627 | A | 8/1989 |
| JP | 4939398 | B1 | 3/2012 |
| KR | 101253541 | | 4/2013 |
| MX | 302238 | | 8/2013 |
| NZ | 576030 | | 10/2012 |
| UA | 99904 | C2 | 10/2012 |
| WO | 198902269 | A1 | 3/1989 |
| WO | 199104667 | A1 | 4/1991 |
| WO | 199428906 | A1 | 12/1994 |
| WO | 199705152 | | 2/1997 |
| WO | 200168099 | A1 | 9/2001 |
| WO | 2003101999 | A2 | 12/2003 |
| WO | 2004045546 | A2 | 6/2004 |
| WO | 2005103056 | A2 | 11/2005 |
| WO | 2006107806 | A2 | 10/2006 |
| WO | 2008045377 | A2 | 4/2008 |
| WO | 2008045378 | A2 | 4/2008 |
| WO | 2012135686 | A1 | 10/2012 |
| WO | 2013082559 | A1 | 8/2013 |

OTHER PUBLICATIONS

Notice of Allowance received for Brazilian Patent Application No. PI0717775-5, dated Aug. 18, 2020, 1 page. (English translation not available).

Martinez et al. "Control of Severe Hyperbillirubinemia in Full-Term Newborns with the Inhibitor of Billirubin Production Sn-Mesoporphyrin" Jan. 1999, Pediatrics 1 03(1):1-5.

Morris "Asymmetric Hydrogenation, Transfer Hydrogenation and Hydrosilyation of Ketones Catalyzed by Iron Complexes" May 28, 2009, Chemical Society Reviews 38:2282-2291.

Non-Final Office Action dated Jan. 30, 2007, for U.S. Appl. No. 10/812,156, filed Mar. 29, 2004, ten pages.

Non-Final Office Action dated Oct. 20, 2003, for U.S. Appl. No. 10/453,815, filed Jun. 3, 2003, three pages.

Non-Final Office Action dated Oct. 22, 2007 for U.S. Appl. No. 11/239,769, filed Sep. 30, 2005, 8 pages.

Non-Final Office Action dated Oct. 23, 2007 for U.S. Appl. No. 11/096,359, filed Apr. 1, 2005, 8 pages.

Notice of Allowability dated Apr. 15, 2010, for U.S. Appl. No. 11/957,317, filed Dec. 14, 2007, 1 page.

Notice of Allowability dated Dec. 19, 2003, for U.S. Appl. No. 10/453,815, filed Jun. 3, 2003, 1 page.

Notice of Allowability dated Sep. 13, 2007, for U.S. Appl. No. 10/812,156, filed Mar. 29, 2004, two pages.

Porter et al. "Hyperbillirubinemia in the Term Newborn" Feb. 15, 2002, American Family Physician 65 (4):599-606.

Reboucas et al. "A Simple, Catalytic H2-hydrogenation Method for the Synthesis of Fine Chemicals; Hydrogenation of Protoporphyrin IX Dimethyl Ester" Jul. 17, 2006, Tetrahedron Letters 47:5119-5122.

Reddy et al. "Tin-mesoporphyrin in the Treatment of Severe Hyperbilirubinemia in a Very-low-birth-weight Infant" 2003, Journal of Perinatology 23:507-508.

Sacerdoti et al. "Role of the Heme Oxygenases in Abnormalities of the Mesenteric Circulation in Cirrhotic Rats" Nov. 4, 2003, The Journal of Pharmacology and Experimental Therapeutics 308(2):636-643.

Shenouda et al. "The Pharmacokinetics (PK) of Stannsoporfin in Healthy Adult Volunteers are Dose-Proportionate" Oct. 2004, American College of Clinical Pharmacology 44:1185-1186.

Simionatto et al. "Studies on the Mechanism of Sn-Protoporphyrin Suppression of Hyperbilirubinemia. Inhibition of Heme Oxidation and Billirubin Production" Feb. 1985, J. Clin. Invest. 75:513-521.

Sisson et al. "Sn-Protoporphyrin Blocks the Increase in Serum Billirubin Levels that Develops Postnatally in Homozygous Gunn Rats" Mar. 1988, J. Exp. Med. 167:1247-1252.

Stokowski "Investigational Drug to Prevent Severe Jaundice" Oct. 2004, Advances in Neonatal Care 4(5):257.

Subcommittee on Hyperbilirubinemia "American Academy of Pediatrics Clinical Practice Guideline: Management of Hyperbilirubinemia in the Newborn Infant 35 or More Weeks of Gestation" Jul. 2004, Pediatrics 114(1):297-316.

Sugihara et al. "Determination of Vanadyl Porphyrins by Demetalation with Hydrogen Bromide-Formic Acid" Nov. 1964, Analytical Chemistry 36(12):2374-2376.

Suresh et al. "Metalloporhyrins for Treatment of Unconjuagated Hyperbillirubinemia in Neonates (Review)" 2003 (e-published Jan. 20, 2003), Cochrane Collaboration of Systematic Reviews 1: 1-15.

Swarbrick "Encyclopedia of Pharmaceutical Technology" 2007, Informa Healthcare USA, Inc. 3rd Ed. 6:3768-3775.

Taylor "Metalloporphyrins. II. Cobalt and Manganese Mesoporphyrins in Coordination with Nitrogenous Bases" Sep. 1, 1940, Journal of Biological Chemistry 135(2):569-595.

Ushio et al. "Asymmetric Reduction of Ortho-Multisubstituted Benzophenones Catalyzed by Diamine-ZN-diol Complexes" Apr. 18, 2005, Tetrahedron Letters 46:2903-2906.

Valaes et al. "Control of Hyperbillirubinemia in Glucose-6-Phosphate Dehydrogenase-deficient Newborns using an Inhibitor of Billirubin Production, Sn-Mesoporphyrin" May 1998, Pediatrics 101(5)1-7.

Valaes et al. "Control of Jaundice in Preterm Newborns by an Inhibitor of Bilirubin Production: Studies With Tin-Mesoporphyrin" Jan. 1994, Pediatrics 93(1): 130-140.

(56) References Cited

OTHER PUBLICATIONS

Varvarigou et al., "Transcutaneous Bilirubin Nomogram for Prediction of Significant Neonatal Hyperbilirubinemia," Sep. 2009, Pediatrics, 124(4), 1052-1059.
Zvedina et al. "Metal Exchange Reactions Between Cadmium Protoporphyrin and Cobalt and Zinc Chlorides in Acetronitrile and Dimethyl Sulfoxide" Jan. 1, 2006, Russian J. ofInorgan. Chem. 51(1):120-125.
Summons to Attend Oral Proceedings dated Jan. 25, 2018 in European Patent Application No. 15185138.3, 5 pages.
Examination Report No. 1 dated May 9, 2018 in Australian Patent Application No. 2017236044, 5 pages.
Examination Report No. 2 dated May 9, 2018 in Australian Patent Application No. 2017236044, 3 pages.
Examination Report dated Dec. 13, 2018 in Canadian Patent Application No. 2,857,153, 4 pages.
Decision to refuse a European patent application dated Dec. 21, 2018 in European Patent Application No. 12854066.3, 4 pages.
Final Office Action dated Apr. 9, 2019 in U.S. Appl. No. 13/691,677, 15 pages.
Extended search report dated Jul. 18, 2019 in European Patent Application No. 19158655.1, 7 pages.
Office Action dated Aug. 1, 2019 in Canadian Patent Application No. 2,857,153, 4 pages.
Goldberg et al., "Use of Stannsoporfin as an Adjuvant to Phototherapy to Prevent Need for Exchange Transfusion In Near-Term and Term Infants", Pediatric Research, vol. 55, No. 5, Suppl. S, Part 2, pp. 459A (Apr. 2004).
American Academy of Pediatrics, Provisional Committee for Quality Improvement and Subcommittee on Hyperbilirubinemia "Practice Parameter: Management of Hyperbilirubinemia in the Healthy Term Newborn" Oct. 1, 1994, Pediatrics 94(4):558-565.
Baker et al. "The Preparation of Mesoporphyrin IX and Etioporphyrin III" Aug. 1964, Analytical Biochemistry 8(4):512-518.
Bauer et al. "Pharmazeutische Technologie" 1993 published by George Thieme Verlag Stuttgart (New York) 4thh Ed. pp. 225-227.
Bauer et al. "Stability-Indicating High Performance Liquid Chromatographic Analysis of Tin Protoporphyrin and Other Free Acid Metalloporphyrins" 1988, Journal of Chromatography 445:429-432.
Bettelheim et al. "Chapter 18. Proteins" 1998, General Organic & Biochemistry, 5th Ed. p. 596.
Bhutan I et al. "Randomized Placebo-Controlled Clinical Trial of Stannsoporfin (Sn-MP) to Prevent Severe Hyperbillirubinemia in Term and Near-Term Infants" Apr. 2004, Pediatric Research Abstract No. 2542.
Breslow et al. "Biochemical Properties of the Heme Oxygenase Inhibitor, Sn-Protoporphyrin" Mar. 5, 1986, The Journal of Biological Chemistry 261 (7):3135-3141.
Cannon et al. "Targeted Delivery of a Heme Oxygenase Inhibitor with a Lyophilized Liposomal Tim Mesoprophyrin Formulation" 1993, Pharmaceutical Research 1 0(5): 715-721.
Corwin et al. "A Synthetic Ferroporphyrin Complex That is Passive to Oxygen" Aug.-Dec. 1946, Journal of the American Chemical Society 68:2473-2478.
Cowan et al. "Synthesis and Properties of Metal-Substituted Myoglobins" May 31, 1989, Inorganic Chemistry 28(11):2074-2078.
Delaney et al. "Photophysical Properties of Sn-Porphyrins: Potential Clinical Implications" Apr. 1988, Pediatrics 81(4):498-504.
Denissen "Synthesis of [119mSn]-Mesoporphyrin IX Dichloride" Dec. 1990, Journal of Labelled Compounds and Radiopharmaceuticals, XXVIII ( 12): 1421-1426.
Drummond "Control of Heme Metabolism by Synthetic Metalloporphyrins" 1987, Annals of New York Academy of Sciences 514:87-95.
Drummond et al. "An Experimental Model of Postnatal Jaundice in the Suckling Rat, Suppression of Induced Hyperbillirubinemia by Sn-Protoprophyrin" Jul. 1984, J. Clin. Invest. 74:142-149.

Drummond et al. "Chemoprevention of Severe Neonatal Hyperbillirubinemia" Oct. 2004, Seminars in Perinatology 28(5):365-368.
Drummond et al. "Prevention of neonatal hyperbillirubinemia by tin Protoporphyrin IX, a potent competitive inhibitor of heme oxidation" Oct. 1981, PNAS USA 78(10):6466-6470.
Drummond et al. "Reduction of the C2 and C4 Vinyl groups of Sn-Protoporphyrin to Form Sn-Mesoporphyrin Markedly Enhances the Ability of the Metalloporphyrin to Inhibit In Vivo Heme Catabolism" May 15, 1987, Archives of Biochemistry and Biophysics 255(1):64-74.
Ellfolk et al. "Separation of Porphyrins by Multiple Liquid-Liquid Partition" 1969, Acta. Chern. Scand. 23(3 part 1):846-858.
Eurasian Search Report dated Sep. 23, 2014 for EU 201400124.
European (Partial) Supplemental Search Report and Written Opinion dated Jun. 9, 2008, for EP 06749109 filed on Mar. 31, 2006, 10 pages.
European Search Report and Written Opinion dated Feb. 22, 2011 for EP 10014149 filed Mar. 31, 2006.
European Search Report and Written Opinion dated Nov. 24, 2010 for EP 10011800 filed Jun. 3, 2003, 6 pages.
European Supplemental Search Report dated Jan. 13, 2012 for EP 11176115 filed on Oct. 4, 2007, 9 pages.
European Supplemental Search Report dated Mar. 30, 2011 for EP 04811883 filed Nov. 24, 2004, 2 pages.
European Supplementary Search Report dated May 18, 2006, for EP 03736811 filed Jun. 3, 2003, 2 pages.
European Supplementary Search Report dated Sep. 12, 2006 for EP 03786815 filed Nov. 18, 2003, 3 pages.
European Supplementary Search Report and Written Opinion dated Aug. 28, 2014 for EP 12765367.
European Search Report and Written Opinion dated Apr. 22, 2015 for EP 12854066.
Galbraith et al. "Pharmacokinetics of Tin-Mesoporphyrin in Man and the Effects of Tin-Chelated Porphyrins of Hyperexcretion of Heme Pathway Precursors in Patients with Acute Inducible Porphyria" Jun. 1989, Hepatology 9 (6):882-888.
Goodman et al. Goodman & Gilman's The Pharmaceutical Basis of Therapeutics, 6th Edition, MacMillan Publishing Co., NY 1980 (TOC).
Hamori et al. "Suppression of Carbon Monoxide Excretion by Zinc Mesoporphyrin in Adult Wistar Rats: Evidence for Potent In Vivo Inhibition of Billirubin Production" Oct. 1988, Research Communications in Chemical Pathology and Pharmacology 62(1):41-48.
Hansen "Kemicterus in Term and Near-Term Infants—The Specter Walks Again" Oct. 2000, Acta Pediatrica 89(10):1155-1157.
Hermann et al. "Heterogeneous Metal-Insertion: a Novel Reaction with Porphyrins" Apr. 15, 1978, Canadian J. Chern. 56(8):1 084-1087.
Holmes et al. "Synthesis of Protoporphyrin81X Derivatives Bearing Extended Propionate Side-Chains" May 29, 2009, Arkivoc 5:5-16.
International Search Report and Written Opinion dated Apr. 3, 2008 for PCT Patent Application No. PCT/US 07/021486 filed on Apr. 10, 2007, 15 pages.
International Search Report and Written Opinion dated Feb. 9, 2007 for PCT Patent Application No. PCT/US04/39240, filed Nov. 24, 2004, six pages.
International Search Report and Written Opinion dated Mar. 27, 2008 for PCT Patent Application No. PCT/US07/21485 filed Oct. 4, 2007, nine pages.
International Search Report and Written Opinion dated May 24, 2007 for PCT Patent Application No. PCT/US06/12185, filed Mar. 31, 2006, eight pages.
International Search Report dated Aug. 31, 2012 for PCT Patent Application No. PCT/US12/31557 filed Mar. 30, 2012.
International Search Report dated Jun. 21, 2004 for PCT Patent Application No. PCT/US03/17426 filed Jun. 3, 2003, two pages.
International Search Report dated May 26, 2004 for PCT Patent Application No. PCT/US03/36885 filed Nov. 18, 2003, two pages.
International Search Report and Written Opinion dated Feb. 8, 2013 for PCT/US2012/067484.
Kaplan et al. "Determination of Isosmolar Blood Anticoagulant Solutions by the Freezing-Point Method" 1957, Clinical Chemistry 4(2): 142-145.

(56) References Cited

OTHER PUBLICATIONS

Kappas et al. "A Method for Interdicting the Development of Severe Jaundice in Newborns by Inhibiting the Production of Billirubin" Jan. 2004, Pediatrics 113:119-123.

Kappas et al. "A Single Dose of Sn-Mesoporphyrin Prevents Development of Severe Hyperbillirubinemia in Glucose-6-Phosphate Dehydrogenase-Deficient Newborns" Jul. 2001, Pediatrics 108:25-30.

Kappas et al. "Direct Comparison of Sn-Mesoporphyrin, An Inhibitor of Bilirubin Production, and Phototherapy in Controlling Hyperbilirubinemia in Term and Near-Term Newborns" Apr. 1995, Pediatrics 95(4):468-474.

Kappas et al. "Sn-Mesoporphyrin Interdiction of Severe Hyperbillirubinemia in Jehovah's Witness Newborns as an Alternative to Exchange Transfusion" Dec. 2001, Pediatrics 1 08(6):1374-1377.

Kappas et al. "Sn-Protoporphyrin Use in the Management of Hyperbillirubinemia in Term Newborns with Direct Coombs-Positive ABO Incompatability" Apr. 1, 1988, Pediatrics 81 (4):485-49T.

Keren et al., "Identifying Newborns at Risk of Significant Hyperbilirubinemia: A Comparison of Two Recommended Approaches," 2005, Arch Dis Child 90: 415-421.

Lomova et al. "Advances in the Synthesis of Complex Compounds or Porphyrins with Highly-Charged Cations of p-, d- and f-" 1993, Koordinatsionnaya Khimiya 19(3):171-184 (with Eng. Translation).

\* cited by examiner

HIGH-PURITY LARGE-SCALE PREPARATION OF STANNSOPORFIN

CROSS REFERENCE TO RELATED APPLICATIONS

This application is a continuation application of U.S. application Ser. No. 16/298,603 filed Mar. 11, 2019, which is a continuation application of U.S. application Ser. No. 15/867,900 filed Jan. 11, 2018, now U.S. Pat. No. 1,0273, 255, issued Apr. 30, 2019, which is a divisional application of U.S. application Ser. No. 15/343,967 filed Nov. 4, 2016, now U.S. Pat. No. 9,902,745, issued Feb. 27, 2018, which is a continuation application of U.S. application Ser. No. 14/793,921, filed Jul. 8, 2015, now U.S. Pat. No. 9,517,239, issued Dec. 13, 2016, which is a continuation of U.S. application Ser. No. 14/460,080, filed Aug. 14, 2014, now U.S. Pat. No. 9,107,927, issued Aug. 18, 2015, which is a continuation of U.S. application Ser. No. 14/019,513, filed Sep. 5, 2013, now U.S. Pat. No. 8,835,416, issued Sep. 16, 2014, which is a continuation of U.S. application Ser. No. 12/968,651, filed Dec. 15, 2010, now U.S. Pat. No. 8,530,458, issued Sep. 10, 2013, which is a continuation of U.S. application Ser. No. 11/867,559, filed Oct. 4, 2007, now U.S. Pat. No. 7,960,371, issued Jun. 14, 2011, which claims the benefit of U.S. Provisional Appln. No. 60/849,641, filed Oct. 4, 2006 and U.S. Provisional Appln. No. 60/904,601, filed Feb. 28, 2007.

TECHNICAL FIELD

This invention pertains to methods for synthesizing stannsoporfin (tin (IV) mesoporphyrin IX dichloride) in large quantities at high purity, and the compositions so produced.

BACKGROUND

Stannsoporfin, or tin (IV) mesoporphyrin IX dichloride, is an inhibitor of the enzyme heme oxygenase. Stannsoporfin has been proposed for therapeutic use in several diseases, such as infant hyperbilirubinemia (U.S. Pat. Nos. 4,657,902; 4,668,670; WO 94/28906) and psoriasis (U.S. Pat. No. 4,782,049). Because of this pharmaceutical utility, methods of preparing stannsoporfin are of great interest.

Infant hyperbilirubinemia (also known as infant jaundice or neonatal hyperbilirubinemia) occurs in a newborn when the liver is unable to conjugate bilirubin so it can be excreted at a rate commensurate with bilirubin formation. Bilirubin comes from the release of heme as part of the physiological conversion from fetal to adult hemoglobin at birth. The enzyme heme oxygenase oxidizes heme to biliverdin; the enzyme biliverdin reductase then reduces the biliverdin to bilirubin. Bilirubin at high serum levels is a neurotoxic substance. In adult humans, the liver rapidly converts bilirubin into a conjugated, excretable form. In newborn humans, however, the liver is still developing, and uptake and conjugation by the liver is not as efficient as in adults. Additionally, hemolysis may be taking place at a greater relative rate than in adults. All of these factors can lead to excessive bilirubin in the infant. For some infants, high serum levels of bilirubin can have detrimental physiological consequences. Bilirubin is yellow, and infants with excess bilirubin appear jaundiced, having a yellow tinge to their skin and to the whites of their eyes.

Infants who have highly elevated serum levels of bilirubin are at risk of developing kernicterus, a rare but potentially devastating neurological disorder which can result in severe life-long disabilities and complications such as athetosis, hearing loss, vision problem, and dental problems. (See Centers for Disease Control and Prevention World-Wide-Web.cdc.gov/ncbddd/dd/kernicterus.htm.) Accordingly, infants should be carefully monitored after birth, and therapeutic intervention should be commenced if an infant's bilirubin level is excessive. The American Academy of Pediatrics has published a Clinical Practice Guideline for evaluating newborns for hyperbilirubinemia and treating at-risk newborns; see Pediatrics 114:297-316 (2004). As health-care costs have risen in the United States, seemingly healthy newborns and their mothers are discharged rapidly, sometimes as quickly as 24 to 48 hours after birth. However, it is believed that this practice may have contributed to an increase in cases of kernicterus, which had been virtually eliminated from developed countries; see Hansen TWR, Acta Paediatr. 89:1155-1157 (2000)). Because early discharge can delay the detection of jaundice and hyperbilirubinemia in infants, effective means of treating hyperbilirubinemia rapidly are desirable. The unique medical status of the newborn also requires that any means of treatment be as safe as possible, as side effects that are tolerable in adults may be completely unacceptable in neonates.

Currently approved and commonly used treatments for hyperbilirubinemia include phototherapy and exchange transfusion. Phototherapy involves irradiating the newborn with light in the 430 to 490 nm range (blue light). The light converts bilirubin into lumirubin and photobilirubin, which are more readily excreted by the infant, and thus can result in a reduction of bilirubin levels.

Stannsoporfin (tin (IV) mesoporphyrin IX dichloride) has been demonstrated to be of therapeutic value in treating hyperbilirubinemia; see Valaes et al., Pediatrics 93:1-11 (1994) and Kappas et al., Pediatrics, 95:468-474 (1995). Other indications in which stannsoporfin can be used are disclosed in U.S. Pat. No. 4,692,440 (to increase the rate of heme excretion), WO 89/02269 (to counteract the toxicity of cancer therapy), U.S. Pat. No. 4,782,049 (to treat psoriasis) and other publications.

U.S. Pat. No. 6,818,763, U.S. Patent Application Publication 2004/0210048, and U.S. patent application Ser. No. 11/096,359 disclose methods of synthesizing stannsoporfin. However, it is still desirable to develop methods to produce stannsoporfin at higher purity, due to the therapeutic advantages of using as pure a substance as possible and also due to the stringent requirements of regulatory agencies.

The current application discloses methods of synthesizing stannsoporfin at a heretofore unachieved level of purity, as well as large-scale preparations of pure stannsoporfin. The current application also discloses a new method of insertion of tin and other metals into porphyrin rings. This new method can significantly decrease the time required for synthesis of stannsoporfin.

DISCLOSURE OF THE INVENTION

The current invention embraces, in certain aspects, high-purity stannsoporfin in large scale (bulk) quantity, and methods for making such compositions of stannsoporfin. The invention also embraces other synthetic methods and chemical compositions as disclosed herein.

In one embodiment, the invention embraces a composition of matter comprising high-purity stannsoporfin in large scale (or bulk) quantity. In another embodiment, the invention embraces a composition of matter comprising high-purity stannsoporfin in large scale (or bulk) quantity when produced in a single batch, that is, a single-batch large scale (or bulk) high-purity amount of stannsoporfin. The high-purity stannsoporfin can be at least about 97% pure, at least about 98% pure, at least about 98.5% pure, at least about 99% pure, at least about 99.5% pure, or at least about 99.8% pure. The amount of any single impurity in the high-purity stannsoporfin can be less than about 0.1%, less than about 0.09%, less than about 0.08%, or about 0.07% or less; in another embodiment, the any single impurity is any single product-related impurity. The large-scale (bulk) amount of stannsoporfin can be at least about 10 grams, at least about 25 grams, at least about 50 grams, at least about 100 grams, at least about 200 grams, at least about 500 grams, at least about 1.0 kg, at least about 2.0 kg, or at least about 5.0 kg. In one embodiment, the high-purity stannsoporfin as variously described above is produced in a single batch.

In an alternative embodiment, the large scale quantity of stannsoporfin is at least about 97% pure, at least about 98% pure, at least about 98.5% pure, at least about 99% pure, at least about 99.5% pure, or at least about 99.8% pure, and has no impurity present in an amount greater than about 0.2%, and more preferably has no impurity present in an amount greater than 0.15%, and still more preferably has no impurity present in an amount greater than 0.12%. In one embodiment, the high-purity stannsoporfin is produced in a single batch.

In additional embodiments, the amount of palladium impurities present in the large-scale amount of high-purity stannsoporfin is less than about 20 ppm, less than about 15 ppm, less than about 10 ppm, or less than about 5 ppm. In one embodiment, the high-purity stannsoporfin is produced in a single batch.

In another embodiment, the invention embraces a method of making high-purity stannsoporfin on a large scale, comprising the steps of: a) exposing a metallic hydrogenation catalyst to a hydrogen atmosphere to form pre-hydrogenated catalyst; and b) contacting hemin with the pre-hydrogenated catalyst and maintaining the hemin and catalyst under one or more combinations of temperature, hydrogen pressure, and time sufficient to remove iron from the hemin and reduce the vinyl groups of the hemin to ethyl groups, thus forming mesoporphyrin IX. In another embodiment, the invention embraces a method of making high-purity stannsoporfin on a large scale, comprising the steps of: a) exposing a metallic hydrogenation catalyst to a hydrogen atmosphere to form pre-hydrogenated catalyst; b) contacting hemin with the pre-hydrogenated catalyst and maintaining the hemin and catalyst under one or more combinations of temperature, hydrogen pressure, and time sufficient to remove iron from the hemin and reduce the vinyl groups of the hemin to ethyl groups, thus forming mesoporphyrin IX; and c) reacting mesoporphyrin IX with a tin (II) salt to form stannsoporfin using a controlled rate of oxidation. In one embodiment, the metallic hydrogenation catalyst comprises palladium, palladium on carbon, platinum, platinum on carbon, nickel, or nickel-aluminum catalyst. In another embodiment, the metallic hydrogenation catalyst is palladium. In another embodiment, the metallic hydrogenation catalyst is palladium on carbon. The method can produce a large-scale amount of high-purity stannsoporfin in a single batch.

In another embodiment, the invention embraces a method of making high-purity stannsoporfin on a large scale, comprising the steps of: a) exposing a metallic hydrogenation catalyst to a hydrogen atmosphere to form pre-hydrogenated catalyst; b) contacting hemin with the pre-hydrogenated catalyst and maintaining the hemin and catalyst under one or more combinations of temperature, hydrogen pressure, and time sufficient to remove iron from the hemin and reduce the vinyl groups of the hemin to ethyl groups, thus forming mesoporphyrin IX; and c) reacting mesoporphyrin IX with tin (II) oxide to form stannsoporfin. In one embodiment, the metallic hydrogenation catalyst comprises palladium, palladium on carbon, platinum, platinum on carbon, nickel, or nickel-aluminum catalyst. In another embodiment, the metallic hydrogenation catalyst is palladium. In another embodiment, the metallic hydrogenation catalyst is palladium on carbon. The method can produce a large-scale amount of high-purity stannsoporfin in a single batch.

In another embodiment, the invention embraces a method of making mesoporphyrin IX, comprising the steps of: a) exposing a palladium on carbon catalyst to a hydrogen atmosphere to form pre-hydrogenated palladium catalyst; and b) contacting hemin with the pre-hydrogenated catalyst and maintaining the hemin and catalyst under one or more combinations of temperature, hydrogen pressure, and time sufficient to remove iron from the hemin and reduce the vinyl groups of the hemin to ethyl groups, thus forming mesoporphyrin IX. In additional embodiments, step b) is carried out at about 80 to 100° C., preferably at about 85 to 90° C., with hydrogen pressure at about 50 to 70 psi, preferably at about 55 to 60 psi, for about 1 to 3 hours, preferably about 1 to 1.5 hours; then at about 40 to 60° C., preferably about 45 to 50° C., with hydrogen pressure at about 50 to 70 psi, preferably at about 55 to 60 psi, for about 18 to 48 hours, preferably about 24 hours.

In another embodiment, the invention embraces a preparation of readily filterable mesoporphyrin IX dihydrochloride, wherein at least about 10 grams can be filtered in less than about 90 minutes, less than about 60 minutes, less than about 45 minutes, less than about 35 minutes, less than about 25 minutes, or less than about 10 minutes, from a solution where the amount of solvent is present in at least about a 50-to-1 ratio by weight to the amount of mesoporphyrin IX dihydrochloride. In another embodiment, the invention embraces a preparation of readily filterable mesoporphyrin IX dihydrochloride, wherein at least about 1000 grams can be filtered in less than about 1 day, less than about 12 hours, less than about 6 hours, less than about 4 hours, less than about 3 hours, or less than about 2 hours, from a solution where the amount of solvent is present in at least about a 50-to-1 ratio by weight to the amount of mesoporphyrin IX dihydrochloride. In one embodiment, the solvent is a mixture of water, hydrochloric acid, and formic acid; the hydrochloric acid can be about 31% hydrochloric acid prior to mixing.

In another embodiment, the invention embraces a method of making a readily filterable mesoporphyrin IX dihydrochloride preparation, comprising the step of adding an aqueous solution of hydrochloric acid to a solution of mesoporphyrin IX formate in formic acid. In one embodiment, the concentration of hydrochloric acid in the aqueous solution is about 0.5 to 2.0 N. In another embodiment, the concentration of hydrochloric acid in the aqueous solution is about 0.75 to 1.25 N. In another embodiment, the concentration of hydrochloric acid in the aqueous solution is about 1.0 N.

In another embodiment, the invention embraces a method of inserting tin into mesoporphyrin IX, comprising reacting the mesoporphyrin IX with a tin salt in the absence of a proton scavenger.

In another embodiment, the invention embraces a method of inserting tin into mesoporphyrin IX, comprising reacting the mesoporphyrin IX with a tin salt at a controlled rate of oxidation. In one embodiment, the mesoporphyrin IX is reacted with a tin salt in a reaction vessel having a headspace, and the rate of oxidation is controlled by introducing an oxygen-containing gas into the headspace of the reaction vessel. In another embodiment, the oxygen-containing gas introduced into the headspace of the reaction vessel is about 3 to 22% oxygen in an inert gas, such as nitrogen. In another embodiment, the oxygen-containing gas introduced into the headspace of the reaction vessel is air. In another embodiment, the oxygen-containing gas introduced into the headspace of the reaction vessel is about 4 to 15% oxygen in an inert gas, such as nitrogen. In another embodiment, the oxygen-containing gas introduced into the headspace of the reaction vessel is about 5 to 10% oxygen in an inert gas, such as nitrogen. In another embodiment, the oxygen-containing gas introduced into the headspace of the reaction vessel is about 6% oxygen in an inert gas, such as nitrogen. In another embodiment, the oxygen-containing gas introduced into the headspace of the reaction vessel is about 6% oxygen in nitrogen.

In any of the above embodiments, the large scale amount of high-purity stannsoporfin can be produced in a single batch.

In any of the above embodiments, the reactants, intermediates, and/or products can undergo additional steps of purification. In some embodiments, the additional purification comprises treating the reactant, intermediate, or product with diatomaceous earth and/or activated carbon. In one embodiment, the treating of the reactant, intermediate, or product with diatomaceous earth and/or activated carbon comprises dissolving or suspending the reactant, intermediate, and/or product in a solvent, adding diatomaceous earth and/or activated carbon, filtering off the diatomaceous earth and/or activated carbon, and recovering the reactant, intermediate, or product from the filtrate. In some embodiments, the additional purification comprises triturating the reactant, intermediate, or product with hot acid, such as about 0.1 to 6N HCl in water, preferably about 3N HCl in water. In some embodiments, one, two, or three of the steps of treating with diatomaceous earth, treating with activated carbon, and triturating with hot acid are performed sequentially, in any order, and can be repeated as desired.

In another embodiment, the invention embraces a method of inserting a metal into a porphyrin compound or a salt thereof using a metal oxide. In another embodiment, the metal cation of the metal oxide is in an intermediate oxidation state. In another embodiment, the porphyrin compound is a mesoporphyrin or salt thereof, or a protoporphyrin or salt thereof, or a hematoporphyrin or salt thereof, or a deuteroporphyrin or salt thereof. In another embodiment, the porphyrin compound is mesoporphyrin IX or a salt thereof. In another embodiment, the porphyrin compound is mesoporphyrin IX dihydrochloride. In another embodiment, the resulting product is a metallated porphyrin or a salt thereof. In another embodiment, the resulting product is a metallated mesoporphyrin or a salt thereof or a metallated protoporphyrin or a salt thereof or a metallated hematoporphyrin or a salt thereof or a metallated deuteroporphyrin or a salt thereof. In other embodiments, the metal oxide is selected from tin oxide, zinc oxide, copper oxide, cadmium oxide, cobalt oxide, chromium oxide, iron oxide, aluminum oxide, titanium oxide, nickel oxide, manganese oxide, silver oxide, gold oxide, vanadium oxide, platinum oxide, antimony oxide, or arsenic oxide. In other embodiments, the metal oxide is selected from tin (II) oxide, zinc (II) oxide, copper (I) oxide, copper (II) oxide, cadmium (II) oxide, cobalt (II) oxide, cobalt (III) oxide, cobalt (IV) oxide, $Co_3O_4$, chromium (II) oxide, chromium (III) oxide, chromium (IV) oxide, chromium (V) oxide, chromium (VI) oxide, iron (II) oxide, iron (III) oxide, $Fe_3O_4$, aluminum (III) oxide, titanium (II) oxide, titanium (III) oxide, titanium (IV) oxide, nickel (II) oxide, manganese (II) oxide, manganese (III) oxide, manganese (IV) oxide, manganese (VII) oxide, silver (I) oxide, silver (II) oxide, gold (I) oxide, gold (III) oxide, vanadium (II) oxide, vanadium (III) oxide, vanadium (IV) oxide, vanadium (V) oxide, platinum (II) oxide, platinum (IV) oxide, antimony (III) oxide, antimony (IV) oxide, antimony (V) oxide, arsenic (III) oxide, or arsenic (V) oxide. In other embodiments, the resulting product is a tin porphyrin, zinc porphyrin, copper porphyrin, cadmium porphyrin, cobalt porphyrin, chromium porphyrin, iron porphyrin, aluminum porphyrin, titanium porphyrin, nickel porphyrin, manganese porphyrin, silver porphyrin, gold porphyrin, vanadium porphyrin, platinum porphyrin, antimony porphyrin, arsenic porphyrin, or a salt thereof. In other embodiments, the resulting product is a tin mesoporphyrin, zinc mesoporphyrin, copper mesoporphyrin, cadmium mesoporphyrin, cobalt mesoporphyrin, chromium mesoporphyrin, iron mesoporphyrin, aluminum mesoporphyrin, titanium mesoporphyrin, nickel mesoporphyrin, manganese mesoporphyrin, silver mesoporphyrin, gold mesoporphyrin, vanadium mesoporphyrin, platinum mesoporphyrin, antimony mesoporphyrin, arsenic mesoporphyrin, or a salt thereof. In other embodiments, the resulting product is a tin mesoporphyrin IX, zinc mesoporphyrin IX, copper mesoporphyrin IX, cadmium mesoporphyrin IX, cobalt mesoporphyrin IX, chromium mesoporphyrin IX, iron mesoporphyrin IX, aluminum mesoporphyrin IX, titanium mesoporphyrin IX, nickel mesoporphyrin IX, manganese mesoporphyrin IX, silver mesoporphyrin IX, gold mesoporphyrin IX, vanadium mesoporphyrin IX, platinum mesoporphyrin IX, antimony mesoporphyrin IX, arsenic mesoporphyrin IX, or a salt thereof. In other embodiments, the resulting product is a tin protoporphyrin, zinc protoporphyrin, copper protoporphyrin, cadmium protoporphyrin, cobalt protoporphyrin, chromium protoporphyrin, iron protoporphyrin, aluminum protoporphyrin, titanium protoporphyrin, nickel protoporphyrin, manganese protoporphyrin, silver protoporphyrin, gold protoporphyrin, vanadium protoporphyrin, platinum protoporphyrin, antimony protoporphyrin, arsenic protoporphyrin, or a salt thereof. In other embodiments, the resulting product is a tin hematoporphyrin, zinc hematoporphyrin, copper hematoporphyrin, cadmium hematoporphyrin, cobalt hematoporphyrin, chromium hematoporphyrin, iron hematoporphyrin, aluminum hematoporphyrin, titanium hematoporphyrin, nickel hematoporphyrin, manganese hematoporphyrin, silver hematoporphyrin, gold hematoporphyrin, vanadium hematoporphyrin, platinum hematoporphyrin, antimony hematoporphyrin, arsenic hematoporphyrin, or a salt thereof. In other embodiments, the resulting product is a tin deuteroporphyrin, zinc deuteroporphyrin, copper deuteroporphyrin, cadmium deuteroporphyrin, cobalt deuteroporphyrin, chromium deuteroporphyrin, iron deuteroporphyrin, aluminum deuteroporphyrin, titanium deuteroporphyrin, nickel deuteroporphyrin, manganese deuteroporphyrin, silver deuteroporphyrin, gold deuteroporphyrin, vanadium deuteroporphyrin, platinum deuteroporphyrin, antimony deuteroporphyrin, arsenic deuteroporphyrin, or a salt thereof.

In another embodiment, the invention embraces a method of inserting tin into a porphyrin compound or a salt thereof using tin (II) oxide. In another embodiment, the porphyrin compound is a mesoporphyrin or salt thereof, or a protoporphyrin or salt thereof, or a hematoporphyrin or salt thereof. In another embodiment, the porphyrin compound is mesoporphyrin IX or a salt thereof. In another embodiment, the porphyrin compound is mesoporphyrin IX dihydrochloride. In another embodiment, the resulting product is a tin (IV) porphyrin or a salt thereof. In another embodiment, the resulting product is a tin (IV) mesoporphyrin or a salt thereof or tin (IV) protoporphyrin or a salt thereof or tin (IV) hematoporphyrin or a salt thereof. In another embodiment, the resulting product is tin (IV) mesoporphyrin IX or a salt thereof.

In another embodiment, the invention embraces a method of inserting tin into a porphyrin compound or a salt thereof by providing a porphyrin compound or salt thereof, providing tin (II) oxide, and contacting the tin (II) oxide with the porphyrin compound or salt thereof under acidic conditions, whereby the tin (II) oxide inserts into the porphyrin ring to yield a tin (IV) porphyrin compound. In another embodiment, the tin (II) oxide is dissolved or suspended in acetic acid or formic acid, preferably acetic acid. In another embodiment, the porphyrin compound or salt thereof is dissolved or suspended in formic acid or acetic acid, preferably formic acid. In another embodiment, the equivalent ratio of the total amount of tin (II) oxide used to the total amount of porphyrin compound or salt thereof used is about two to six, preferably about four. In another embodiment, the solution or suspension of the porphyrin compound or salt thereof is added dropwise to the tin (II) oxide solution. The dropwise addition can take place over a period of about three to nine hours, preferably over about six hours. The tin (II) oxide solution or suspension is maintained at a temperature of about 25-115° C., preferably about 50-75° C., more preferably about 60-65° C.

In another embodiment, the invention embraces a method of inserting tin into a porphyrin compound or a salt thereof (such as mesoporphyrin IX or a salt thereof, such as mesoporphyrin IX dihydrochloride) by providing a mesoporphyrin compound or salt thereof (such as mesoporphyrin IX or a salt thereof, such as mesoporphyrin IX dihydrochloride), providing tin (II) oxide, and contacting the tin (II) oxide with the mesoporphyrin compound or salt thereof (such as mesoporphyrin IX or a salt thereof, such as mesoporphyrin IX dihydrochloride) under acidic conditions, whereby the tin (II) oxide inserts into the porphyrin ring (such as a mesoporphyrin IX ring) to yield a tin (IV) porphyrin compound. In another embodiment, the tin (II) oxide is dissolved or suspended in acetic acid or formic acid, preferably acetic acid. In another embodiment, the mesoporphyrin compound or salt thereof (such as mesoporphyrin IX or a salt thereof, such as mesoporphyrin IX dihydrochloride) is dissolved or suspended in formic acid or acetic acid, preferably formic acid. In another embodiment, the equivalent ratio of the total amount of tin (II) oxide used to the total amount of mesoporphyrin compound or salt thereof (such as mesoporphyrin IX or a salt thereof, such as mesoporphyrin IX dihydrochloride) used is about two to six, preferably about four. In another embodiment, the solution or suspension of the porphyrin compound or salt thereof (such mesoporphyrin IX or a salt thereof, such as mesoporphyrin IX dihydrochloride) is added dropwise to the tin (II) oxide solution. The dropwise addition can take place over a period of about three to nine hours, preferably over about six hours. The tin (II) oxide solution or suspension is maintained at a temperature of about 25-115° C., preferably about 50-75° C., more preferably about 60-65° C. After completion of the dropwise addition, the reaction mixture can be maintained at a temperature of about 60 to 65° C. for about 18 to 24 additional hours. The reaction mixture can be cooled and filtered after the additional reaction time.

In another embodiment, the invention embraces a method for producing a tin (IV) porphyrin compound or salt thereof comprising a) preparing a solution or suspension of an unmetallated porphyrin compound or a salt thereof; b) preparing a solution or suspension of tin (II) oxide, wherein steps (a) and (b) can occur in any order or simultaneously; and c) contacting the solution or suspension of tin (II) oxide with the solution or suspension of unmetallated porphyrin compound or salt thereof under conditions suitable to form the tin (IV) porphyrin compound or salt thereof. The solution or suspension of tin (II) oxide and the solution or suspension of unmetallated porphyrin compound or salt thereof can be independently prepared with formic acid or acetic acid; for example, the solution or suspension of tin (II) oxide can be prepared with acetic acid, and the solution or suspension of unmetallated porphyrin compound or salt thereof can be prepared with formic acid. The unmetallated porphyrin compound is selected from mesoporphyrins, protoporphyrins, hematoporphyrins, and salts thereof, such as mesoporphyrin IX or a salt thereof, such as mesoporphyrin IX dihydrochloride. The contacting step c) can comprise adding the solution or suspension of unmetallated porphyrin compound or salt thereof in a dropwise manner to the solution or suspension of tin (II) oxide under conditions suitable to form the tin (IV) porphyrin compound or salt thereof. The adding in a dropwise manner can completed within about 3 to 9 hours, such as about 6 hours. The solution or suspension of tin (II) oxide can be maintained at a temperature of about 60 to 65° C. during the adding in a dropwise manner. After completion of the adding of the solution or suspension of unmetallated porphyrin compound or salt thereof in a dropwise manner to the solution or suspension of tin (II) oxide, the reaction mixture can be maintained at a temperature of about 60 to 65° C. for about 18 to 24 additional hours. The reaction mixture can be cooled and filtered after the additional reaction time. In another embodiment, the method for producing a tin (IV) porphyrin compound or salt thereof is performed in the absence of a proton scavenger or proton sponge.

The tin (IV) mesoporphyrin produced by any of the methods described above can undergo additional steps of purification. In some embodiments, the additional purification comprises treating the tin (IV) mesoporphyrin with diatomaceous earth and/or activated carbon. In one embodiment, the treating of the tin (IV) mesoporphyrin with diatomaceous earth and/or activated carbon comprises dissolving or suspending the tin (IV) mesoporphyrin in a solvent, adding diatomaceous earth and/or activated carbon, filtering off the diatomaceous earth and/or activated carbon, and recovering the tin (IV) mesoporphyrin from the filtrate. In some embodiments, the additional purification comprises triturating the tin (IV) mesoporphyrin with hot acid, such as about 0.1 to 6N HCl in water, preferably about 3N HCl in water, at a temperature of about 60 to 95° C., preferably about 80 to 95° C., more preferably about 85 to 90° C. In some embodiments, one, two, or all three of the steps of treating with diatomaceous earth, treating with activated carbon, and triturating with hot acid are performed sequentially, in any order, and can be repeated as desired.

In another embodiment, the invention embraces stannsoporfin as produced by any of the processes described herein.

In another embodiment, the invention embraces high-purity stannsoporfin in large scale (or bulk) quantity, wherein said high-purity stannsoporfin is stable for at least about three months or at least about six months under storage. In another embodiment, the high-purity stannsoporfin in large quantity is prepared as a single batch. In another embodiment, the invention embraces high-purity stannsoporfin in large scale (or bulk) quantity, wherein said high-purity stannsoporfin retains its high purity for at least about three months or at least about six months under storage. In another embodiment, the storage conditions are about 25° C. and about 60% relative humidity. In another embodiment, the storage conditions are shout 40° C. and about 75% relative humidity. In another embodiment, the stannsoporfin is stored in a polyethylene bag. In another embodiment, the stannsoporfin is stored in a polyethylene bag within another polyethylene bag. In another embodiment, the double-bagged stannsoporfin is stored in a high-density polyethylene drum. In another embodiment, each polyethylene bag is about 4 mils thick (about 4/1000 of an inch, or about 0.1 millimeter).

In another embodiment, the invention embraces a method of treating infant hyperbilirubinemia, comprising administering stannsoporfin to a patient in need of said treatment, where the stannsoporfin was produced in high purity and on a large scale. In another embodiment, the stannsoporfin is produced as a single batch.

In another embodiment, the invention embraces a method of preventing infant hyperbilirubinemia, comprising administering stannsoporfin to a patient in need of said prevention, where the stannsoporfin was produced in high parity and on a large scale. In another embodiment, the stannsoporfin is produced as a single batch.

DETAILED DESCRIPTION OF THE INVENTION

In one embodiment of the current invention, stannsoporfin is prepared in large quantity at high purity. In another embodiment of the current invention, stannsoporfin is prepared in large quantity at high purity, wherein the large quantity is prepared as a single batch. Stannsoporfin (tin (IV) mesoporphyrin IX dichloride; Chemical Abstracts Registry Number 106344-20-1) is also known by the trade name Stanate®, which is a registered trademark of InfaCare Pharmaceutical Corp., Plymouth Meeting, Pa. Stannsoporfin has the following structure:

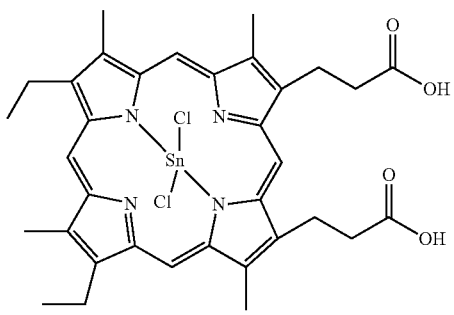 [SMILES: CCC1=C(C)/C2=C/c3c(CC)c(C)c4[n]3[Sn]([Cl])([Cl])[n]3/c(c(C)c(CCC(=O)O)/c3=C/C3=NC(=C\4)/C(C)=C3CCC(=O)O)=C\C1=N2]

having molecular formula $C_{34}H_{36}Cl_2N_4O_4Sn$ and molecular weight 754.29.

By "large quantity," "large scale," or "bulk" is meant at least about 10 grams. Other quantities for large scale production of stannsoporfin are at least about 25 grams, at least about 50 grams, at least about 100 grams, at least about 200 grams, at least about 500 grams, at least about 1.0 kg, at least about 2.0 kg, or at least about 5.0 kg.

By "single batch" is meant that the amount of the product specified is synthesized at one time. A single batch is typically produced after a reaction (or series of reactions) is carried out once (note that a single preparation of the compound subjected as a whole to one or more reactions repeatedly, such as repeated purifications, is considered a single batch). A single batch thus excludes multiple preparations of a compound carried out at separate times, or in divided amounts, which are later combined.

By "high purity" is meant a preparation that meets both of the following two criteria: 1) the overall level of purity is at least about 97%; that is, the desired product (stannsoporfin) accounts for at least 97% of the preparation; and 2) any individual product-related impurity present is present in an amount of less than about 0.1% of the preparation. The purity is preferably measured by HPLC analysis. A "product-related" impurity is an impurity that requires characterization by the guidelines of the United States Food and Drug Administration; accordingly, components of the drug product such as water are not considered an impurity.

By "unmetallated porphyrin" is meant a porphyrin lacking a metal ion coordinated by one or more pyrrole nitrogens. A "metallated porphyrin" is a porphyrin having a metal ion coordinated by at least one pyrrole nitrogen.

By "intermediate oxidation state" is meant an element, such as a metal, which is present in an oxidation state intermediate between its neutral (uncharged, or zero oxidation state) and its most highly oxidized state. By way of non-limiting example, iron typically forms oxidation states of (0), (II), and (III); the (II) oxidation state (ferrous state) is an intermediate oxidation state.

The purity of the preparation is important for use of the compound as a pharmaceutical. The overall level of purity can be at least about 97%, at least about 98%, at least about 98.5%, at least about 99%, or at least about 99.5%. A high-purity preparation is also defined, as above, as a preparation with the additional condition that any individual impurity present is present in an amount of less than about 0.1% of the preparation. (Note that the total amount of impurities may exceed 0.1%—for example, one impurity may be present at 0.08%, and another at 0.07%, totaling 0.15%—but when measured individually, no impurity is present at amounts equal to or exceeding about 0.1%.) In another embodiment, any individual impurity present is present in an amount of less than about 0.09%. In another embodiment, any individual impurity present is present in an amount of less than about 0.08% or less. In another embodiment, any individual impurity present is present in an amount of about 0.07% or less. Water can be present in the preparation, even in significant amounts (at least about 1% to 5%), but it not considered an impurity. Other residual solvents, such as acetone, formic acid, and acetic acid, are also not considered impurities, especially if they occur at or below the permissible levels described in the guidelines of the International Conference on Harmonisation of Technical Requirements for Registration of Pharmaceuticals for Human Use, ICH Harmonised Tripartite Guideline—Impurities: Guideline for Residual Solvents, Q3C(R3), Step 4 version, November 2005 (World-Wide-Web.ich.org/LOB/media/MEDIA423.pdf).

In an alternate embodiment, the stannsoporfin has no impurity present in an amount greater than about 0.2%, and more preferably has no impurity present in an amount greater than 0.15%, and still more preferably has no impurity present in an amount greater than 0.12%.

The current synthesis produces stannsoporfin meeting the two criteria listed under high-purity above (overall purity of at least about 97%, without treating water or residual solvents as impurities, and any individual impurity present is present in an amount of about 0.1% or less). The second criterion, regarding the level of individual impurities, is of interest due to regulatory requirements. The Food and Drug Administration of the United States of America typically requires detailed characterization of impurities at a level equal to 0.1%, while impurities present at a level below 0.1% need not be characterized in detail unless they have unusually potent pharmacological or toxic effects at a level of less than 0.1% (see the publications *Guidance for Industry: ANDAs: Impurities in Drug Substances,* U.S. Department of Health and Human Services, Food and Drug Administration, Center for Drug Evaluation and Research (CDER), November 1999; available at World-Wide-Web-site-.fda-.gov/cder/guidance/2452fnl.htm; and *Guidance for Industry Q3A Impurities in New Drug Substances,* United States Department of Health and Human Services, Food and Drug Administration, Center for Drug Evaluation and Research (CDER) and Center for Biologics Evaluation and Research (CBER), February 2003 ICH, Revision 1, available at World-Wide-Web-site-.fda.gov/cder/guidance/4164fnl.pdf). By meeting these threshold conditions set by the Food and Drug Administration, the high-purity material has significant advantages over material of lower purity from the regulatory standpoint.

Another advantage of the invention as described herein is the expected reproducibility of the synthesis, providing the ability to generate repeated batches of high-purity stannsoporfin in large quantity. Another advantage of the invention as described herein is the ability of the process and product to meet requirements for Good Manufacturing Practice (GMP), as defined by law, regulation, or regulatory agency requirements in various countries (for example, current Good Manufacturing Practice as specified in the United States Code of Federal Regulations, Title 21, Sections 210 and 211).

Another advantage of the invention as described herein is the production of high-purity bulk amounts of stannsoporfin in a single batch, with concomitant advantages of increased homogeneity, lower synthetic cost, and relative ease of characterization.

Synthesis of Stannsoporfin at High Purity

As porphyrins are light-sensitive compounds, the starting materials, intermediates, products, and solutions or suspensions thereof should be protected from light exposure, and stored in a dark location in light-excluding containers.

Synthesis of stannsoporfin proceeds with hemin (iron (III) protoporphyrin IX chloride) as a starting material. The quantities required for large-scale synthesis are obtained from porcine red blood cells. Hemin DMF grade is purchased from Harimex (Loenen, The Netherlands); the material is used without purification prior to use (purity as supplied is greater than about 98% by HPLC). The hemin is heated in organic solvent with a hydrogenation catalyst on carbon under a hydrogen atmosphere. This reductive step serves both to remove the Fe ion from the porphyrin ring, and to reduce the protoporphyrin IX vinyl groups to ethyl groups (thus converting the protoporphyrin IX into mesoporphyrin IX), as indicated in the following scheme.

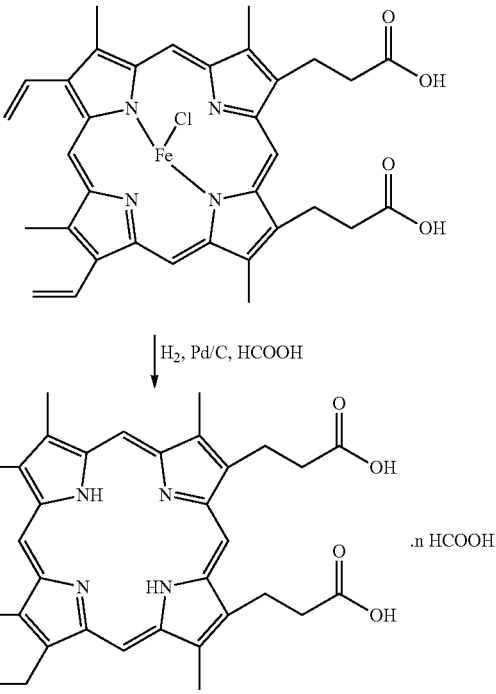

A preferred hydrogenation catalyst is palladium on carbon, used in an amount of about 0.0135 to 0.0165 equivalents, preferably about 0.015 equivalents. Other suitable catalysts can be used, including palladium metal particles, platinum on carbon, platinum metal particles, nickel, or nickel-aluminum catalyst, provided that residual amounts of catalyst in the product meet pharmaceutical specifications. The nickel-aluminum catalyst can be RANEY nickel (RANEY is a registered trademark of W. R. Grace & Co., New York, N.Y.). A preferred organic solvent is formic acid.

It was discovered that pre-treatment of the Pd/C catalyst with hydrogen gas prior to addition of hemin to the reaction reduces palladium impurities and thus contributes to the overall purity of the final stannsoporfin product. Without pro-hydrogenation of the catalyst prior to hemin addition, residual palladium levels of about 50 ppm were detected in the product, which is significantly above the product specifications of less than about 20 ppm residual palladium. With the pre-hydrogenation step, residual palladium was reduced to undetectable levels (less than about 5 ppm residual palladium). Accordingly, the improved synthesis provides for levels of residual palladium levels in the product tin (IV) mesoporphyrin IX dichloride of less than about 20 ppm palladium, preferably less than about 15 ppm palladium, more preferably less than about 10 ppm palladium, still more preferably less than about 5 ppm palladium. The pre-hydrogenation of the catalyst can be performed under a hydrogen atmosphere of about 15 to 75 psi (about 1 to 5 bar; about 100,000 to 500,000 Pascals), preferably about 30 to 50 psi (about 2 to 3.5 bar; about 200,000 to 350,000 Pascals), more preferably about 40 psi (about 2.75 bar or 275,000 Pascals). The temperature for pre-hydrogenation of the catalyst can vary between about 25 to 60° C., preferably about 35 to 50° C., more preferably about 40 to 45° C. The time period for pre-hydrogenation of the catalyst can range from about 2 to 48 hours, preferably from about 6 to 24 hours, more preferably from about 8 to 16 hours, still more preferably about 12 hours.

Thus, typically, the catalyst is added to the chemical reactor first, followed by the formic acid solvent (for example, about 17.5 to 22.5 parts solvent, preferably about 20 parts solvent). Before addition of solvent, the hydrogen can be evacuated and the reactor can be filled with a nitrogen atmosphere for safety reasons. Upon completion of formic acid addition, the nitrogen atmosphere is replaced by a hydrogen atmosphere, at, for example, about 40 pounds per square inch (approximately 2.75 bar or 275,000 Pascals). The temperature is then adjusted to about 35 to 50° C. preferably about 40 to 45° C., for approximately 8 to 24 hours, preferably about 12 hours, prior to introduction of the hemin starting material into the reactor. The prehydrogenated catalyst suspension is then cooled, followed by addition of hemin (in solvent) to the reactor. The hydrogen atmosphere is evacuated during the introduction of hemin for safety purposes, leaving only the hydrogen associated on the Pd/C catalyst. The reactor is re-pressurized to about 30 to 35 psi with hydrogen, and the reaction is agitated at about 20 to 25° C. for about 30 minutes. The reaction is then warmed to about 80 to 100° C., preferably to about 85 to 90° C., with vigorous agitation, and hydrogen pressure is increased to about 50 to 70 psi (about 3.4 to 4.8 bar or about 340,000 to 480,000 Pascals), preferably about 55 to 60 psi (about 3.8 to 4.2 bar or about 380,000 to 420,000 Pascals). The reaction temperature is maintained for about 1 to 3 hours, preferably about 1 to 1.5 hours. The reaction is then cooled to about 40 to 60° C., preferably to about 45 to 50° C., and hydrogen pressure maintained and hydrogenation continued for about 18 to 48 hours, preferably 20 to 30 hours, more preferably about 24 hours.

The reaction is then cooled and depressurized with evacuation of hydrogen from the reactor. Diatomaceous earth (such as HYFLO SUPERCEL, a registered trademark of Celite Corp., Santa Barbara, Calif.), activated carbon (such as DARCO KB, a registered trademark of NORIT Americas, Inc., Marshall, Tex.), and solvent are added to the reactor. The suspension is filtered, and the filter cake is washed with solvent. This treatment serves to remove residual iron and residual palladium from the material.

The filtrate is concentrated by distillation under vacuum (which can be performed at room temperature, or at lower temperatures, such as at approximately 10 to 15° C.) to remove excess solvent. A precipitant, for example, an ether such as methyl t-butyl ether (MTBE), is then added, over a period of at least about 30 seconds to at least about 3 hours, preferably over a period of at least about 1 hour, to the concentrated solution. When MTBE is added, it can be added in about 17.5 to 22.5 parts, preferably in about 20 parts.

The suspension can be cooled to a temperature of about −15 to −30° C., preferably to about −20 to −25° C.

The suspension is filtered and the filtercake rinsed with an organic solvent, such as ethers, including methyl t-butyl ether (MTBE), diethyl ether, or diisopropyl ether. After filtration is complete and the cake is rinsed, the material is then dried in a vacuum oven at a temperature not exceeding about 60° C., for example, from about 45 to 60° C.

When prepared using formic acid as the solvent, the resulting product, mesoporphyrin IX, is precipitated out as a formate salt; this is the preferred form for isolation of the mesoporphyrin IX after the hydrogenation step. After additional purification steps, the mesoporphyrin IX formate is converted into a hydrochloride salt. This step provides a further purification of the intermediate. In addition, the presence of proton scavengers such as formate (or other organic anions, such as acetate) during the subsequent tin insertion step has been shown to result in higher levels of impurities than if such scavengers are excluded. Accordingly, it is preferred to replace the formate anion of mesoporphyrin IX formate with an anion less capable of scavenging protons or buffering the solution during the tin insertion step; such anions include chloride and other halide anions such as bromide or iodide.

When the intermediate isolated from the hydrogenation step is mesoporphyrin IX formate, it is placed in a reaction vessel with diatomaceous earth, activated carbon, and formic acid, (for example, with about 10% w/w diatomaceous earth, about 20% w/w activated carbon, and about 10 parts formic acid) to undergo additional purification. The suspension is agitated at, for example, about 20 to 30° C., preferably at about 20 to 25° C., for about 1.5 to 2.5 hours. The suspension is then filtered, and the filtercake washed with formic acid, for example, about 5 parts of formic acid. The resulting filtrate solution is then concentrated down to about 5 to 6 parts volume. Another vessel is charged with purified water and 31% hydrochloric acid to prepare about 15 parts of approximately 1N hydrochloric acid. Approximately 6 parts of this HCl solution is transferred into the vessel containing about 6 parts of the filtrate, preferably at a temperature of about 20 to 25° C. and over a period of at least about 60 minutes. The solution is then seeded with mesoporphyrin IX dihydrochloride (available from earlier syntheses) and agitated, preferably for at least about 2 hours. The remaining 9 parts of 1N hydrochloric acid is transferred into the vessel under vigorous agitation, preferably over a period of at least 60 minutes. The suspension is then further agitated at about 20 to 30° C., preferably at about 20 to 25° C., for about 2 to 3 hours. It is then filtered, and rinsed with purified water. The product is dried on the filter under a stream of nitrogen.

In earlier processes, the step above was carried out by re-dissolving solid mesoporphyrin IX formate in formic acid, and then adding the formic acid solution to the hydrochloric acid in order to convert the mesoporphyrin IX formate to the mesoporphyrin IX dihydrochloride. However, filtration of the mesoporphyrin IX dihydrochloride so produced was found to be quite slow on a pilot plant scale, requiring up to five days to complete, and the subsequent drying on the filter then took between about two to three weeks. An improvement in the process was developed; as described above, the 1N hydrochloric acid solution is added into the formic acid solution of mesoporphyrin IX formate. This has been discovered to result in mesoporphyrin IX dihydrochloride that can be filtered more rapidly. Addition of seed material can also be performed during the procedure, for example, at the beginning of the addition of the 1N HCl into the formic acid solution of mesoporphyrin IX formate, or during the addition of 1N HCl into the formic acid solution of mesoporphyrin IX formate, such as when about 10%, about 20%, about 30%, about 40%, about 50%, about 60%, about 70%, about 80%, or about 90% of the 1N HCl has been added to the formic acid solution of mesoporphyrin IX formate. Preferably, as in the process as described immediately above, the seed material is added after 40% of the 1N HCl has been added to the formic acid solution of mesoporphyrin IX formate. The addition of the seed material can also aid in the formation of a product which can be filtered more quickly. Since the mesoporphyrin IX dihydrochloride resulting from these process improvements can be filtered much more quickly, on the order of hours or even minutes instead of days, significant savings in time and cost are achieved. Thus, in another embodiment, the time for filtration of at least about 10 grams of mesoporphyrin IX dihydrochloride is reduced to less than about 90 minutes, less than about 60 minutes, less than about 45 minutes, less than about 35 minutes, less than about 25 minutes, or less than about 10 minutes. In a further embodiment, the time for filtration of at least about 1000 grams of mesoporphyrin IX dihydrochloride is reduced to less than about 1 day less than about 12 hours, less than about 6 hours, less than about 4 hours, less than about 3 hours, or less than about 2 hours.

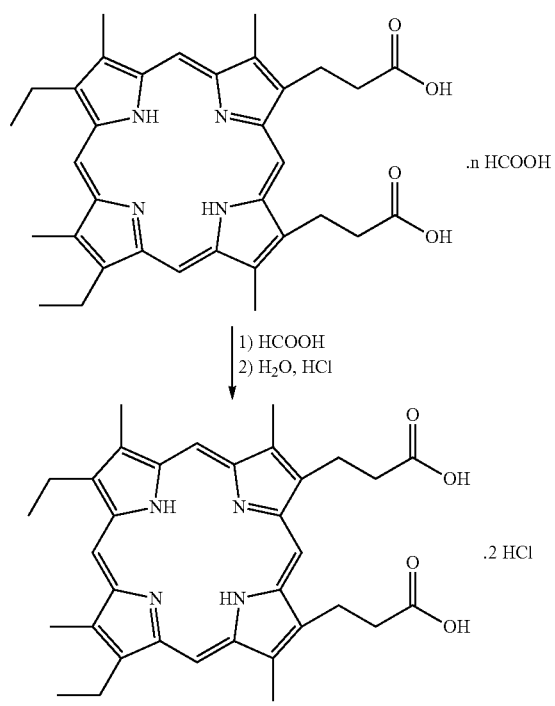

Conversion Mesoporphyrin IX Hydrochloride to Stannsoporfin (Tin (IV) Mesoporphyrin IX) Via Treatment with Tin (II) Salt The mesoporphyrin IX hydrochloride is then treated with a tin(II) salt, such as $SnCl_2$ in an organic solvent, such as acetic acid, under oxidizing conditions, which yields the desired product, tin (IV) mesoporphyrin IX dichloride (stannsoporfin). For example, mesoporphyrin IX dihydrochloride and tin (II) chloride are placed in a vessel, and acetic acid is added at about 20 to 30° C., preferably at about 20 to 25° C. The suspended reagents are agitated for at least about 30 minutes. With vigorous agitation, the mixture is warmed under an inert atmosphere (such as nitrogen or argon) to reflux.

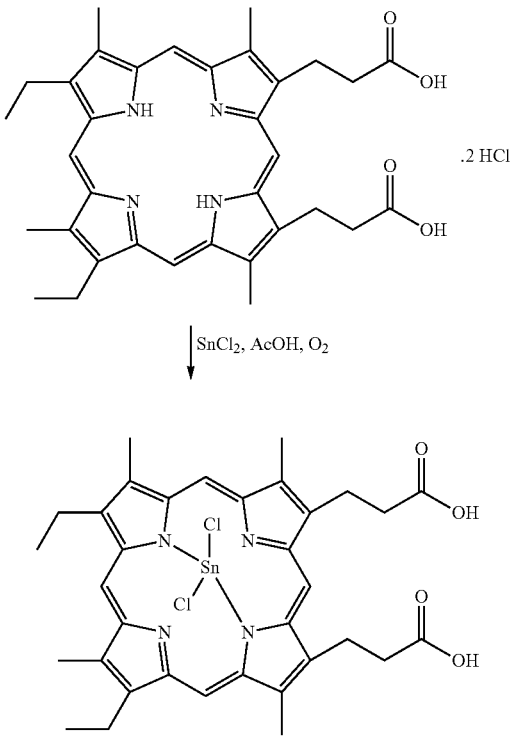

Once reflux has commenced, an atmosphere of approximately 6% oxygen in nitrogen is introduced into the headspace of the vessel. The gas can be from about 3% to about 22% oxygen; about 6% is preferred to minimize explosion hazards. The mixture is kept at reflux for about 100 to 130 hours. The use of the 6% oxygen in nitrogen atmosphere in the headspace instead of sparging or bubbling the gas mixture through the liquid has been found to be advantageous for increasing the yield of tin (IV) mesoporphyrin IX dichloride. Tin (II) can enter the porphyrin ring to complex with the nitrogens, and can also leave the porphyrin ring. However, tin (IV) which is not already bound to the nitrogens of the porphyrin ring cannot enter the ring to complex with the nitrogens. In order to generate tin (IV) mesoporphyrin IX, the tin (II) ion must enter the porphyrin ring, and then undergo oxidation to tin (IV) in situ. Excessively rapid oxidation of the tin (II) ion will cause the insertion reaction to stall, which can lower yields significantly. Accordingly, proper control of the rate of oxidation is needed. Introducing oxygen into the mixture via the interface between the solvent and the oxygen/nitrogen headspace atmosphere provides this control and leads to a reasonable rate of reaction with a good yield of final product.

The reaction mixture can optionally be sampled during the tin insertion step by lowering the temperature to about 50 to 70° C., preferably about 55 to 60° C., removing a sample, and returning the reaction to reflux.

After the tin insertion step, the reaction mixture is cooled, and WFI (water for injection) grade water is added. The suspension is then filtered, and the filter cake washed with WFI water. The filter cake is then placed under vacuum for a minimum of 4 hours to remove residual water.

Conversion of Mesoporphyrin IX Dihydrochloride to Stannsoporfin (Tin (IV) Mesoporphyrin IX) Via Treatment with Tin (II) Oxide

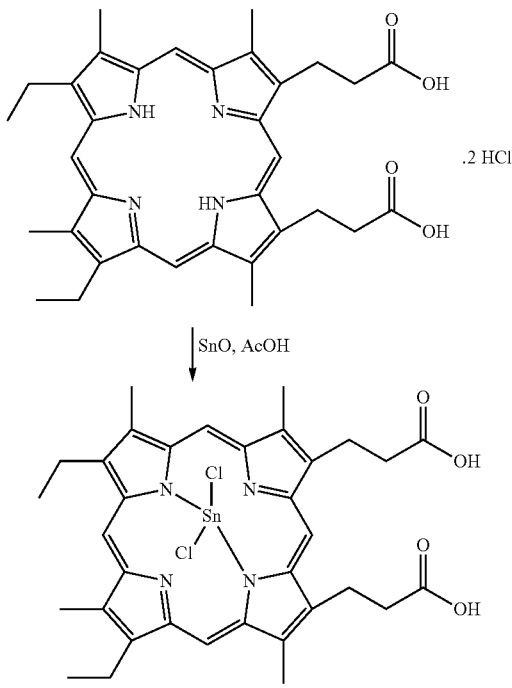

Tin can also be inserted into the mesoporphyrin IX ring via treatment of mesoporphyrin IX dihydrochloride with tin (II) oxide. This reaction can proceed to completion in as short a time as two hours, compared to the four days to three weeks required for tin insertion using the tin (II) salt method described above. A solution/suspension mesoporphyrin IX dihydrochloride in a suitable solvent, for example, formic acid or acetic acid, is added to a solution/suspension of tin (II) oxide in a suitable solvent, for example, acetic acid or formic acid. An exemplary procedure is described below, and also in the Examples.

The mesoporphyrin IX dihydrochloride is dissolved/suspended in formic acid at ambient temperature. As the solution or suspension will have a deep purple color, it is advantageous to pulverize the mesoporphyrin IX dihydrochloride into as fine a powder as possible to aid in dissolution.

The tin (II) oxide is suspended in acetic acid at ambient temperature and stirred. After prolonged stirring, the tin oxide suspension may transform into a gel, which was not observed to affect the reaction adversely. The gel breaks up once the addition of mesoporphyrin IX dihydrochloride commences. The amount of tin (II) oxide is about two equivalents to about six equivalents per equivalent of mesoporphyrin IX dihydrochloride; preferably, about four equivalents of tin (II) oxide are used per equivalent of mesoporphyrin IX dihydrochloride. (In this reaction, the equivalent ratio is the same as the molar ratio.)

The tin (II) oxide solution is maintained at a temperature of about 25-115° C., preferably about 50-75° C., more preferably about 60-65° C. The solution of mesoporphyrin IX dihydrochloride is then added over a period of about three to nine hours, preferably over a period of about six hours. The solution of mesoporphyrin IX dihydrochloride can be at ambient temperature during the addition, or can be maintained at a temperature of about 50-75° C., such as about 60-65° C., during addition. The reaction mixture is maintained at about 25-115° C., preferably about 50-75° C., more preferably about 60-65° C., for about an additional 2 to 48 hours, preferably about an additional 16 to 30 hours, more preferably about an additional 18 to 24 hours, such as about an additional 18 hours or about an additional 24 hours. After the additional reaction time, the suspension is cooled to room temperature (about 20-25° C.), agitated or stirred for at least about five minutes, preferably at least about one hour, and filtered.

General Metal Insertion into Porphyrins Using Metal Oxides

The procedure used for tin insertion into porphyrin rings using metal oxides can also be applied to insertion of other metals using metal oxides. Particularly useful metal oxides are metal oxides where the metal cation of the metal oxide is in an intermediate oxidation state. The procedure can be used for porphyrin compounds or salts thereof, including, but not limited to, a mesoporphyrin or a salt thereof, mesoporphyrin IX or a salt thereof, mesoporphyrin IX dihydrochloride, a protoporphyrin or a salt thereof, a hematoporphyrin or a salt thereof, or a deuteroporphyrin or a salt thereof, to yield the metallated porphyrin compound (or a salt thereof).

Metal oxides which can be used include, but are not limited to, tin oxide, zinc oxide, copper oxide, cadmium oxide, cobalt oxide, chromium oxide, iron oxide, aluminum oxide, titanium oxide, nickel oxide, manganese oxide, silver oxide, gold oxide, vanadium oxide, platinum oxide, antimony oxide, arsenic oxide, tin (II) oxide, zinc (II) oxide, copper (I) oxide, copper (II) oxide, cadmium (II) oxide, cobalt (II) oxide, cobalt (II) oxide, cobalt (IV) oxide, $Co_3O_4$, chromium (II) oxide, chromium (III) oxide, chromium (IV) oxide, chromium (V) oxide, chromium (VI) oxide, iron (II) oxide, iron (III) oxide, $Fe_3O_4$, aluminum (III) oxide, titanium (II) oxide, titanium (III) oxide, titanium (IV) oxide, nickel (II) oxide, manganese (II) oxide, manganese (III) oxide, manganese (IV) oxide, manganese (VII) oxide, silver (I) oxide, silver (II) oxide, gold (I) oxide, gold (III) oxide, vanadium (II) oxide, vanadium (III) oxide, vanadium (IV) oxide, vanadium (V) oxide, platinum (II) oxide, platinum (IV) oxide, antimony (III) oxide, antimony (IV) oxide, antimony (V) oxide, arsenic (III) oxide, or arsenic (V) oxide.

Other porphyrin compounds and tetrapyrroles can also be metallated using the procedures described herein, including, but not limited to, porphyrins such as deuteroporphyrins and deuteroporphyrin IX 2,4-bis(ethylene glycol) (8,13-bis(1,2-dihydroxyethyl)-3,7,12,17-tetramethyl-21H,23H-porphine-2,18-dipropionic acid). Additional porphyrin compounds which can be metallated using the procedures described herein include, but are not limited to, coproporphyrins, cytoporphyrins, etioporphyrins, hematoporphyrins, mesoporphyrins, phylloporphyrins, protoporphyrins, pyrroporphyrins, rhodoporphyrins, uroporphyrins, and phytoporphyrins. A comprehensive listing of porphyrin compounds is given at World-Wide-Web.chem.qmul.ac.uk/iupac/tetrapyrrole/; the porphyrins described therein are hereby incorporated by reference herein as porphyrins which can be metallated using the procedures described herein.

Purification of Tin (IV) Mesoporphyrin IX Dichloride: Hot Acid Trituration

At this point, the crude tin (IV) mesoporphyrin IX dichloride is then triturated with hot acid in order to remove impurities. The material is re-suspended in hydrochloric acid (approximately 0.5 N to 2.0 N, preferably 1 N) and the temperature raised to about 75 to 100° C. or about 80 to 100° C., preferably about 85 to 95° C., more preferably to about 85 to 90° C., for about one to two hours with moderate agitation. The suspension is then cooled to about 20 to 30° C., preferably to about 20 to 25° C., and filtered; the filtercake is rinsed with purified water and dried on the filter under a nitrogen stream.

Purification Tin (IV) Mesoporphyrin IX Dichloride: Treatment at High pH

The material from the hot acid trituration step is combined with diatomaceous earth, activated carbon, water, and ammonium hydroxide. The temperature is adjusted to about 20 to 30° C., preferably to about 20 to 25° C., and agitated, preferably for about 1 to 2 hours. A sample is taken to ensure that the pH is at or above approximately 9. The mixture is then agitated, preferably for about 1 to 2 hours further. The mixture is then filtered. Any material remaining on the filter is rinsed with water; the filtercake is then discarded.

Re-Acidification of Tin (IV) Mesoporphyrin IX Dichloride

The filtrate is then transferred into a mixture of acetic acid and 31% hydrochloric acid, and the mixture is adjusted to about 20 to 30° C., preferably to about 20 to 25° C. The resultant suspension is agitated, preferably for about 15 minutes, sampled to ensure that the pH is less than or equal to about 1, and then agitated again, preferably for about an additional 1 to 2 hours. The suspension is then filtered, and the filtercake rinsed with water, followed by removal of residual water under vacuum.

At this stage, the filtercake is sampled for residual starting material, mesoporphyrin IX dihydrochloride. If the level is above about 0.1%, the high pH treatment followed by re-acidification is repeated as necessary (for example, an addition 1, 2, or 3 times).

Additional Hot Acid Trituration of Tin (IV) Mesoporphyrin IX Dichloride

The filtercake from the previous step is re-suspended in a mixture of approximately two parts by weight WFI grade water and approximately one part by weight 31% HCl, at about 20 to 30° C., preferably at about 20 to 25° C. Under moderate agitation, the mixture is adjusted to about 80 to 100° C., preferably to about 85 to 90° C., for about 6 to 48 hours, preferably about 12 to 24 hours, more preferably about 16 to 18 hours, followed by cooling to about 20 to 30° C., preferably to about 20 to 25° C., for at least about 1 hour. The suspension is filtered, the filtercake rinsed with an aqueous solution of hydrochloric acid (for example, about 1 part 31% HCl to 25 parts WFI grade water, w/w), and dried under a stream of nitrogen (at or below about 50° C.).

The final hot acid treatment serves in order to re-set the form of the stannsoporfin to monomer. In neutral solution, stannsoporfin is in a monomer-dimer equilibrium; treatment with strong acid shifts the equilibrium strongly to the monomer form.

Development work on the stannsoporfin synthesis indicates that for optimum results, the hydrogenation catalyst should be pre-hydrogenated prior to introduction of the hemin starting material; the isolation of the mesoporphyrin IX dihydrochloride from the mesoporphyrin IX formate in formic acid should proceed by addition of the HCl solution to the formic acid solution; the presence of proton scavengers should be avoided during the tin insertion step; and the introduction of the oxygen during the tin insertion step should proceed via introduction of the oxygen/nitrogen mixture to the headspace of the reaction, rather than bubbling or sparging of the gas through the solution. With these optimum parameters in mind, other variables such as temperature, reaction time, reagent concentration, and order of reagent addition can be manipulated to some extent, for example, concentration and reaction time can be varied within about 50 to 200% of the values indicated, or within about 75 to 150% of the values indicated, and temperature can be varied about 5 to 10° C. of the values indicated, to the extent that the variation does not result in large-scale synthesis of stannsoporfin at less than high purity as defined herein. Purification and precipitation steps can be repeated as necessary in order to maintain high purity of the large scale preparation of stannsoporfin.

Therapeutic Use of Stannsoporfin for Treatment or Prevention of Infant Hyperbilirubinemia and Other Diseases Stannsoporfin as produced by the invention can be used for treatment or prevention of infant hyperbilirubinemia (infant jaundice) (see U.S. Pat. Nos. 4,657,902; 4,668,670; and WO 94/28906). Additional methods of using stannsoporfin are disclosed in U.S. Pat. No. 4,692,440 (to increase the rate of heme excretion), WO 89/02269 (to counteract the toxicity of cancer therapy), U.S. Pat. No. 4,782,049 (to treat psoriasis), and other publications. Treatment or prevention of infant hyperbilirubinemia is accomplished by dissolving the stannsoporfin in a pharmaceutically acceptable vehicle. The stannsoporfin is preferably provided in a solution which can be buffered to maintain a suitable pH. Buffers which can be used include phosphate, citrate, gluconate, lactate, tartrate, glycinate, glycylglycinate, bicarbonate, carbonate, maleate, or acetate, with sodium, potassium, magnesium, calcium, or aluminum present as the cation. Histidine and imidazole can also be used as buffers. Phosphate buffers are preferred, particularly sodium phosphate buffer. Buffers must be pharmaceutically acceptable for use as an injectable agent in neonates. The pH of the solution for administration is preferably between about 7.0 to 8.0, more preferably about 7.2 to 7.9, still more preferably about 7.4. The osmolarity of the solution is preferably a or near physiological osmolarity; a preferred range is between about 280 mOsm/L and 310 mOsm/L. Stannsoporfin is preferably administered by injection, more preferably by intramuscular injection. The stannsoporfin is administered in an amount sufficient to treat or prevent infant hyperbilirubinemia, typically about 4.5 mg/kg birthweight; U.S. patent application Ser. No. 11/867,581 filed on Oct. 4, 2007, and International (Patent Cooperation Treaty) Patent Application No. PCT/US07/021486 filed on Oct. 4, 2007, both of which claim priority to U.S. Provisional Patent Application No. 60/849,509, filed on Oct. 4, 2006, disclose a method of treating infant hyperbilirubinemia using lower doses of stannsoporfin, such as 1.5 mg/kg birthweight or 3.0 mg/kg birthweight.

U.S. Pat. No. 6,818,763, U.S. Patent Application Publication 2004/0210048, and U.S. patent application Ser. No. 11/096,359 are specifically hereby incorporated by reference herein in their entirety.

The following examples are intended to illustrate the invention, and are not intended to limit the invention in any manner.

EXAMPLES

Example 1

Exemplary Synthesis of High-Purity Stannsoporfin

Initial Conversion of Hemin to Mesoporphyrin IX

A 200 L glass lined vessel, pressure-rated to 150 psi, is charged with 0.6 kg of 5% palladium on carbon and 73 kg of formic acid. With vigorous agitation, the reactor is pressurized with hydrogen to 60-65 psi and warmed to 40-45° C. for a minimum of 12 hours. With moderate agitation, the reaction is cooled to 20-25° C., the hydrogen atmosphere is evacuated, and the reactor charged with 6.0 kg of hemin (DMF grade) and 73 kg formic acid. The reactor is pressurized to 30-35 psi with hydrogen and agitated at 20-25° C. for 30 minutes.

With vigorous agitation the reaction is warmed to 85-90° C. Hydrogen pressure is then increased to 55-60 psi. The pressure and temperature are maintained for a period of 1-1.5 hours.

The reaction is cooled to 45-50° C. and the hydrogenation is continued at 55-60 psi for 24 hours. The reaction is then cooled to 20-25° C., depressurized and sampled.

The reaction is warmed to 45-50° C., pressurized to 55-60 psi with hydrogen, and agitated a further 6 hours. The reaction is then cooled to 20-25° C., depressurized and sampled again.

Hydrogen is evacuated from the vessel, which is then charged with 3.0 kg HYFLO SUPERCEL, 2.3 kg DARCO KB and 42 kg formic acid. The suspension is filtered, and the filter cake is rinsed with 122 kg formic acid.

A portion of the filtrate is transferred to a 200 L glass lined vessel, cooled to 10-15° C. and distilled under vacuum to remove formic acid. Once the residual volume has dropped to 25-35 L, the remainder of the filtrate is transferred in and distillation continued to a residual volume of 25-30 L.

The reaction to temperature is adjusted to 20-25° C. and 89 kg of methyl tert-butyl ether is added over a minimum of 1 hour. The resultant suspension is agitated at 20-25° C. for 2 hours prior to cooling to −25 to −20° C. for a period of 4 hours.

The suspension is filtered and rinsed with 12 kg of methyl tert-butyl ether. The intermediate product is dried in a vacuum oven at 60° C. or less.

Purification of Mesoporphyrin IX Formate with Diatomaceous Earth and Activated Carbon; Conversion of Mesoporphyrin IX Formate to Mesoporphyrin IX Dihydrochloride The intermediate is transferred to a 50 L glass lined vessel with 10% w/w DARCO KB, 20% w/w HYFLO SUPERCEL and 10 parts formic acid. The suspension is agitated at 20-25° C. for a period of 1.5-2.5 hours.

The suspension is filtered into a second 50 L glass lined vessel. The filtercake is rinsed with 5 parts formic acid and discarded. The filtrate solution is vacuum distilled to a residual volume of 5-6 parts.

A third vessel is clamed with purified water and 31% hydrochloric acid to prepare 15 parts of 1N hydrochloric acid. Six parts of the filtrate solution is transferred into the reactor at 20-25° C. over a minimum of 60 minutes.

The solution is seeded with mesoporphyrin IX dihydrochloride and agitated for a minimum of 2 hours. With vigorous agitation, the remaining 9 parts of 1N hydrochloric acid is transferred into the vessel over a minimum of 1 hour.

The resultant suspension is agitated at 20-25° C. for a period of 2-3 hours prior to isolation by filtration. The filtercake is rinsed with 4 parts of purified water. The intermediate product mesoporphyrin IX dihydrochloride is dried on the filter under a stream of nitrogen.

Conversion Mesoporphyrin IX Dihydrochloride to Tin (IV) Mesoporphyrin IX Dihydrochloride (Stannsoporfin)

A 50 L glass lined vessel is charged with 1.57 kg of mesoporphyrin IX dihydrochloride, 1.862 kg of tin (II) chloride, and 40.9 kg acetic acid at 20-25° C. With moderate agitation, the suspension is maintained at 20-25° C. for a minimum of 30 minutes.

With vigorous agitation, under nitrogen, the mixture is warmed to reflux (ca. 115° C.). Once reflux has been attained, a 6% oxygen in nitrogen atmosphere is introduced to the headspace of the vessel. The reaction mixture is maintained at reflux for a period of 100-130 hours.

The reaction mixture is cooled to 55-60° C. and sampled for residual mesoporphyrin; while awaiting results, the reaction mixture is warmed back to reflux. Once complete, the reaction is cooled to 60-70° C. and charged with 15.7 kg of WFI (water for injection) grade water. The temperature of the suspension is adjusted to 20-25° C. over 30 minutes and agitated for a period of 1 hour.

The suspension is filtered, and the vessel and cake are rinsed with 6.3 kg of WFI water. Upon completion of the wash, the cake is placed under vacuum for a minimum of 4 hours to remove residual water.

A 50 L glass lined vessel is charged with the wet filtercake, 22.4 kg purified water, and 3.7 kg 31% hydrochloric acid at 20-25° C. With moderate agitation, the temperature of the mixture is adjusted to 85-90° C. for a period of 1-2 hours, followed by cooling to 20-25° C. The suspension was filtered and the filtercake rinsed with 6.3 kg purified water. The product is dried on the filter under a stream of nitrogen and packaged.

Purification of Tin (IV) Mesoporphyrin IX Dichloride (Stannsoporfin) at High pH with Diatomaceous Earth and Activated Carbon A 50 L glass lined vessel is charged with 1.448 kg of tin (IV) mesoporphyrin IX dichloride, 0.194 kg HYFLO SUPERCEL, 0.066 kg DARCO KB, 14.5 kg WFI water, and 1.0 kg ammonium hydroxide 26 Be. The temperature of the reaction mixture is adjusted to 20-25° C. and agitated for a period of 1-2 hours. A sample is taken to verify that the pH is ≥9. The mixture is then agitated a further 1-2 hours. The mixture is filtered through into a glass receiver. The cake rinsed with 2.9 kg of water and discarded.

A second 50 L glass lined vessel is charged with 38.2 kg of acetic acid and 2.6 kg of 31% HCl. The temperature is adjusted to 20-25° C. The filtrate from the glass receiver is transferred into the second 50 L vessel over a minimum of 45 minutes at 20-25° C. The glass receiver and transfer apparatus are rinsed with 2.1 kg WFI water into the vessel. The resultant suspension is agitated at 20-25° C. for 15 minutes prior to taking a sample to verify that the pH is ≤1. The suspension is then agitated a further 1-2 hours.

The suspension is filtered, and the vessel and cake are rinsed with 1.3 kg of WFI water. Upon completion of the wash, the cake is placed under vacuum for a minimum of 4 hours to remove residual water.

A sample of the filtercake is taken for testing. If the residual starting material (mesoporphyrin IX dihydrochloride) is at an acceptable level, the reaction proceeds to the next step, otherwise the entire treatment is repeated (i.e., the filtercake is re-dissolved using ammonium hydroxide as above).

Treatment of Tin (IV) Mesoporphyrin IX Dichloride (Stannsoporfin) at Low pH to Set to Monomer Form The wet filtercake is returned to the 50 L glass lined vessel which is then charged with 20.4 kg WFI water and 10.2 kg 31% hydrochloric acid at 20-25° C. With moderate agitation, the temperature of the mixture is adjusted to 85-90° C. for a period of 16-18 hours, followed by cooling to 20-25° C. for a minimum of 1 hour. The suspension is filtered and the filtercake rinsed with a pre-mixed solution of 0.5 kg 31% hydrochloric acid in 12.8 kg WFI water. The product is dried on the filter at <50° C. under a stream of nitrogen and packaged.

Example 2

Alternative Tin Insertion Step Using Tin (II) Oxide as Tin Source

The insertion of tin into mesoporphyrin IX to produce stannsoporfin can be carried out by an alternate synthetic route using tin (II) oxide as the reagent for tin introduction.

A dark, 1000 ml, three-necked, round-bottom flask equipped with a magnetic stirbar, Claisen head, addition funnel, thermometer, condenser, and nitrogen bubbler was charged with 8.4 g tin (II) oxide, and 200 ml acetic acid, at 20-25° C., to form a gray suspension. The suspension was warmed to 60-65° C. under nitrogen.

A separate 250 ml one-neck, round-bottom flask equipped with a stirbar was charged with 10 g mesoporphyrin IX dihydrochloride, and 50 ml formic acid. The mixture was agitated at 20-25° C. for 30 minutes to effect dissolution, resulting in about 60 ml of a deep purple suspension solution at 20-25° C. (Because of the colored solution, complete dissolution is difficult to observe visually; the mesoporphyrin IX dihydrochloride should be thoroughly milled prior to formic acid addition.)

The mesoporphyrin IX dihydrochloride solution was charged to the addition funnel and added dropwise to the tin (II) oxide/acetic acid suspension/solution over a period of 6 hours, while maintaining the temperature of the tin (II) oxide/acetic acid suspension/solution at 60-65° C. The volume in the flask increased from 200 ml to 260 ml; the appearance of the reaction changed from a gray suspension (or white gel), to a purple suspension, to a red suspension.

Once the addition was complete, the reaction was agitated under nitrogen atmosphere at 60-65° C. for a further 18-24 hours. Then 100 ml water was added dropwise over 20-40 minutes, while maintaining the temperature at 60-65° C. The resultant red suspension (about 360 ml) was cooled to 20-25° C. over 30 minutes and agitated for a minimum of 1 hour, followed by filtration under reduced pressure (total filtration time was about 10-20 minutes). The filtercake was rinsed with two portions of 20 ml water. The filtrate volume of about 400 ml was a claret-colored solution; the filtercake mass of about 40-50 g was also claret-colored.

The wet filtercake was carefully broken up into pieces and charged back into the reaction flask with 100 ml 1N HCl. The resultant claret-colored suspension was warmed to 85-95° C. for 1 hour. The suspension was then cooled to 20-25° C. and filtered under reduced pressure (total filtration time was about 20-30 minutes); the filtrate was dark claret to brown in color. The claret-colored filtercake was rinsed with two portions of 20 ml water, dried under a nitrogen stream, and further dried under high vacuum at 80-90° C. for 24 hours. In various repetitions of the synthesis, the yield of product varied from 16.5-21.2 g (70-90%).

Example 3

Analysis of High-Purity Stannsoporfin Made by Exemplary Synthesis Utilizing Tin (II) Chloride as Tin Source Batches of stannsoporfin were prepared using the exemplary synthesis essentially as outlined above in Example 1, as well as earlier methods (see U.S. Pat. No. 6,818,763 and US 2004/0210048).

Basic HPLC analysis is performed using a C-18 column (Zorbax Extend C-18, 4.6×150 mm, 3.5 um particle size, or the equivalent). The detector is set at 400 nm. Solvents (acetonitrile, methanol, and water) are HPLC grade. The mobile phase is 16% acetonitrile:40% methanol:44% 0.5M ammonium acetate, pH 5.15. (The ammonium acetate solution is prepared by dissolving 38.5 g ammonium acetate in 440 mL $H_2O$, and adjusting the pH to 5.15 with acetic acid. Both the ammonium acetate and acetic acid are reagent grade. 160 mL acetonitrile and 400 mL methanol are then added; the mobile phase solution is mixed, filtered, and degassed prior to use.) The flow rate is 1.0 ml/minute. Samples and standards of stannsoporfin are prepared for injection at a concentration of 0.04 mg/mL in 1N NaOH. As stannsoporfin and related compounds are light sensitive, solutions containing stannsoporfin, starting materials, or impurity standards should be kept in opaque containers, and handling and analysis should be conducted under reduced light conditions. Samples and standard solutions should be used within 12 hours of preparation. 5 uL of analyte solution is injected, and a 10-minute run time is used. The retention time of stannsoporfin is typically about 4.8 minutes. The column temperature is maintained at 60° C. After analysis, the column is washed with 80% methanol and 20% water for at least 1 hour at 1.0 mL/min.

HPLC analysis for quantitation of impurities is performed using an ACE 5 C-18 column, 4.6×250 mm, 5 um particle size, with detection at 400 nm. Protection of light-sensitive samples and standards is practiced as described above. The mobile phases used are A: 30% methanol, 70% water with 0.02M ammonium acetate, pH 9.1, and B: 80% methanol, 20% water with 0.02M ammonium acetate, pH 9.1 (mobile phase A is prepared by dissolving 3.0 g of ammonium acetate in 1400 mL water, adjusting pH to 9.1 with $NH_4OH$, and adding 600 mL methanol; mobile phase B is prepared by dissolving 3.0 g of ammonium acetate in 400 mL water, adjusting pH to 9.1 with $NH_4OH$, and adding 1600 mL methanol; mobile phases are mixed, filtered, and degassed prior to use). Samples are dissolved in 0.5% v/v TEA in water at a concentration of approximately 0.2 mg/mL. Samples and standard solutions should be used within 12 hours of preparation.

The analysis is performed using the following gradient conditions:

| Time | % A | % B |
| --- | --- | --- |
| 0 | 100 | 0 |
| 50 | 70 | 30 |
| 65 | 70 | 30 |
| 90 | 0 | 100 |
| 110 | 0 | 100 |
| 111 | 100 | 0 |
| 120 | 100 | 0 | where the concentrations are changed linearly between the points shown.

Table 1 contains a comparison of the HPLC analysis of the product of the current synthesis, column C, as compared to analyses of products from earlier syntheses in column A and column B. Peaks detected are listed in order of retention time relative to stannsoporfin, with the retention time of stannsoporfin set to 1. The batch analyzed in column A was produced in a quantity of 1.1 kg; the batch analyzed in column C was also produced in a quantity of 1.1 kg.

TABLE 1

Analysis of various preparations of stannsoporfin

| Relative Retention Time | A | B | C |
|---|---|---|---|
| 0.33 | 0.06% | | |
| 0.51 | 0.05% | 0.05% | 0.07% |
| 0.55 | | | 0.06% |
| 0.73 | 0.14% | 0.05% | 0.05% |
| 0.76 | 0.07% | | 0.05% |
| 0.83 | 0.05% | | |
| 0.84 | 0.05% | | |
| 0.92 | 0.26% | 0.06% | |
| 0.95 | 0.30% | | 0.05% |
| 0.96 | | 0.22% | |
| 1 | 98% | 99% | 100% |
| 1.05 | 0.09% | | |
| 1.26 | 0.06% | | |

As seen from Table 1, the current stannsoporfin synthesis in column C resulted in material which resulted in a high purity product, of overall purity >99% and which does not contain any impurities at or above 0.1%.

Example 4

Analysis of High-Purity Stannsoporfin Made by Exemplary Synthesis Utilizing Tin (II) Oxide as Tin Source Three batches of stannsoporfin were made using the tin insertion step as described in Example 2. Analysis of the three batches indicated that the purity of stannsoporfin produced was 99.7%, 99.7%, and 99.6% (total content of stannsoporfin was 96.4%, 99.1%, and 97.2%, respectively).

HPLC analysis was performed on a Zorbax Extend C-18 column, 4.6×150 mm, 5 μm thickness. The eluents used were: A: 80% 0.05 M Ammonium Acetate, pH 5.15 with Acetic Acid: 20% Acetonitrile; B: 90% Methanol: 10% Acetonitrile. The temperature used was 40° C. A flow rate of 1.2 ml/min was used, with detection at 400 nm. The retention time of stannsoporfin was 8.8 min, while that of mesoporphyrin IX was 23.1 min, with use of the following gradient listed in Table 2.

TABLE 2

| Time | A | B |
|---|---|---|
| 0.0 | 60 | 40 |
| 10.0 | 25 | 75 |
| 30.0 | 25 | 75 |
| 31.0 | 60 | 40 |
| 40.0 | 60 | 40 |

More extensive analyses of two batches of stannsoporfin produced using the tin oxide insertion method were conducted. These analyses are detailed in Table 3 (batch weight 0.840 kg) and Table 4 (batch weight 1.364 kg) below (where a/a indicates ratio of area of HPLC peaks).

TABLE 3

| Test | Method | Results |
|---|---|---|
| Total Purity | HPLC | Total impurities < 1% a/a; impurity at RRt 0.72 = 0.06% a/a; no other impurity > 0.05%, a/a |
| Water Content | Karl Fischer, coulometric | Trace < 1% w/w |
| Residual Solvents-Acetone | Chromatographic (GC-headspace) | Not detected < 0.1% w/w |
| Organic content-formic acid + acetic acid | HPLC | 0.1% w/w |
| Inorganic content-palladium and iron | Inductively coupled plasma-optical emission spectroscopy | Pd = 5 ppm Fe = 5 ppm |
| Inorganic content-free tin | Differential Pulse Polarography | <0.1% free tin |
| Inorganic content-tin | Inductively coupled plasma-optical emission spectroscopy | 144500 ppm |
| Inorganic content-chloride | Elemental analysis | 104100 ppm |

TABLE 4

| Test | Method | Results |
|---|---|---|
| Total Purity | HPLC | Total impurities < 1% a/a; impurity at RRt 0.72 = 0.06% a/a; no other impurity > 0.05% a/a |
| Water Content | Karl Fischer, coulometric | Trace <1% w/w |
| Residual Solvents-Acetone | Chromatographic (GC-headspace) | Not detected < 0.1% w/w |
| Organic content-formic acid + acetic acid | HPLC | Not detected < 0.1% w/w |
| Inorganic content-palladium and iron | Inductively coupled plasma-optical emission spectroscopy | Pd = 5 ppm Fe = 67 ppm |
| Inorganic content-free tin | Differential Pulse Polarography | <0.1% free tin |
| Inorganic content-tin | Inductively coupled plasma-optical emission spectroscopy | 165000 ppm |
| Inorganic content-chloride | Elemental analysis | 103300 ppm |

Example 5

Stability of High-Purity Stannsoporfin Preparations

The long-term stability of the compound was studied under two different storage conditions: 25° C. (+/−2° C.) and 60% relative humidity (+/−5%); and 40° C. (+/−2° C.) and 75% relative humidity (+/−5%). Primary packaging for the compound was a 4-mil polyethylene bag and secondary packaging for the compound was a 4 mil polyethylene bag, stored in an HDPE drum.

Table 5 and Table 6 show stability data for the batch described in Table 3, under the 25° C./60% RH and 40° C./75% RH conditions, respectively. Table 7 and Table 8 show stability data for the batch described in Table 4 under the 25° C./60% RH and 40° C./75% RH conditions, respectively. Data for the zero-month time point was taken from the batch release analysis (the zero time point represents the actual date when samples were placed in the stability test chambers). The samples were analyzed at approximately 3 months and approximately 6 months after the samples were placed under the storage conditions.

TABLE 5

| Test | 0 months | 3 months | 6 months |
|---|---|---|---|
| Appearance | Red powder free from visual evidence of contamination | Red powder free from visual evidence of contamination | Red powder free from visual evidence of contamination |
| HPLC purity (total impurities) | 0.3 | 0.22 | 0.24 |
| HPLC purity (impurity peak at RRt retention time 0.72-0.73) | 0.06% | <0.05% | 0.07% |
| HPLC assay (w/w, solvent-free anhydrous basis) | 100.7% | 99.8% | 98.4% |
| HPLC assay (w/w as is) | 100.4% | 99.6% | 98.2% |
| Water content (Karl Fischer, coulometric) | Trace < 1% | <1% (0.1%) | <1% (0.1%) |

TABLE 6

| Test | 0 months | 3 months | 6 months |
|---|---|---|---|
| Appearance | Red powder free from visual evidence of contamination | Red powder free from visual evidence of contamination | Red powder free from visual evidence of contamination |
| HPLC purity (total impurities) | 03 | 0.28 | 0.26 |
| HPLC purity (impurity peak at RRt retention time 0.72-0.73) | 0.06% | <0.05% | 0.06% |
| HPLC assay (w/w, solvent-free anhydrous basis) | 100.7% | 101.2% | 99.8% |
| HPLC assay (w/w as is) | 100.4% | 100.9% | 99.6% |
| Water content (Karl Fischer, coulometric) | Trace <1% | <1% (0.2%) | <1% (0.1%) |

TABLE 7

| Test | 0 months | 3 months | 6 months |
|---|---|---|---|
| Appearance | Red powder free from visual evidence of contamination | Red powder free from visual evidence of contamination | Red powder free from visual evidence of contamination |
| HPLC parity (total impurities) | 0.22 | 0.29 | 0.19 |
| HPLC purity (impurity peak at RRt retention time 0.72-0.73) | 0.06% | 0.05% | 0.05% |
| HPLC assay (w/w, solvent-free anhydrous basis) | 102.3% | 102.1% | 98.5% |
| HPLC assay (w/w as is) | 102.3% | 102.0% | 98.4% |
| Water content (Karl Fischer, coulometric) | Trace < 1% | <1% (0.1%) | <1% (0.1%) |

TABLE 8

| Test | 0 months | 3 months | 6 months |
|---|---|---|---|
| Appearance | Red powder free from visual evidence of contamination | Red powder free from visual evidence of contamination | Red powder free from visual evidence of contamination |
| HPLC purity (total impurities) | 0.22 | 0.29 | 0.24 |
| HPLC purity (impurity peak at RRt retention time 0.72-0.73) | 0.06% | <0.05% | 0.06% |
| HPLC assay (w/w, solvent-free anhydrous basis) | 102.3% | 101.1% | 97.8% |
| HPLC assay (w/w as is) | 102.3% | 101.0% | 97.7% |
| Water content (Karl Fischer, coulometric) | Trace < 1% | <1% (0.1%) | <1% (0.1%) |

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A composition comprising stannsoporfin, wherein the stannsoporfin is at least about 97% pure, and wherein any individual impurity is present in an amount less than about 0.08%, the stannsoporfin formed by: a) contacting a solution or suspension of tin (II) oxide with a mesoporphyrin IX or salt thereof under conditions suitable to form a crude stannsoporfin; and b) purifying the crude stannsoporfin to form the stannsoporfin.

2. The composition of claim 1, wherein the composition comprises palladium in an amount of less than about 20 ppm.

3. The composition of claim 1, wherein the composition comprises palladium in an amount of less than about 10 ppm.

4. The composition of claim 1, wherein the composition comprises at least about 10 grams of stannsoporfin.

5. The composition of claim 1, wherein the composition comprises at least about 100 grams of stannsoporfin.

6. The composition of claim 1, wherein the stannsoporfin is a single-batch preparation of stannsoporfin.

7. The composition of claim 1, wherein the stannsoporfin is at least about 98.5% pure.

8. The composition of claim 1, wherein any impurity present is present in an amount of about 0.07% or less.

9. The composition of claim 1, wherein the purifying the crude stannsoporfin comprises a hot acid trituration, followed by treatment at high pH at or above pH 9 followed by re-acidification, and subsequent hot acid trituration.

10. The composition of claim 1, wherein the mesoporphyrin IX of salt thereof is formed by contacting hemin with a pre-hydrogenated catalyst.

11. The composition of claim 10, wherein the pre-hydrogenated catalyst is formed by exposing a metallic hydrogenation catalyst to a hydrogen atmosphere.

12. The composition of claim 1, wherein the mesoporphyrin IX or salt thereof comprises mesoporphyrin IX dihydrochloride.

13. The composition of claim 1, wherein the composition further comprises at least one impurity in an amount between about 0.05% and about 0.08%, the at least one impurity having a relative retention time of 0.72-0.73 in an HPLC analysis.

14. A composition comprising stannsoporfin, wherein the stannsoporfin is at least about 97% pure, and wherein any individual impurity is present in an amount less than about 0.08%, the stannsoporfin formed by: a) exposing a metallic hydrogenation catalyst to a hydrogen atmosphere to form a pre-hydrogenated catalyst; b) contacting hemin with the pre-hydrogenated catalyst to form a mesoporphyrin IX or salt thereof; c) contacting a solution or suspension of tin (II) oxide with the mesoporphyrin IX or salt thereof under conditions suitable to form a crude stannsoporfin; and d) purifying the crude stannsoporfin via hot acid trituration, followed by treatment at high pH at or above pH 9 followed by re-acidification, and subsequent hot acid trituration to form the stannsoporfin.

15. The composition of claim 14, wherein the metallic hydrogenation catalyst comprises palladium on carbon.

16. The composition of claim 14, wherein the mesoporphyrin IX or salt thereof comprises mesoporphyrin IX dihydrochloride.

17. The composition of claim 14, wherein the composition comprises palladium in an amount of less than about 20 ppm.

18. The composition of claim 14, wherein the composition comprises palladium in an amount of less than about 10 ppm.

19. The composition of claim 14, wherein the composition comprises at least about 10 grams of stannsoporfin.

20. The composition of claim 14, wherein the stannsoporfin is at least about 98.5% pure.

* * * * *